United States Patent
Getts et al.

(10) Patent No.: US 11,802,151 B2
(45) Date of Patent: Oct. 31, 2023

(54) BRAIN-SPECIFIC ANGIOGENESIS INHIBITOR 1 (BAI1) ANTIBODIES AND USES THEREOF

(71) Applicant: Code Biotherapeutics, Inc., Hatfield, PA (US)

(72) Inventors: Robert Getts, Hatfield, PA (US); Jessica Bowers, Hatfield, PA (US); Mindy Ellen George-Weinstein, Philadelphia, PA (US); Jacquelyn Gerhart, Philadelphia, PA (US)

(73) Assignee: Code Biotherapeutics, Inc., Hatfield, PA (US)

( * ) Notice: Subject to any disclaimer, the term of this patent is extended or adjusted under 35 U.S.C. 154(b) by 0 days.

(21) Appl. No.: 17/088,256

(22) Filed: Nov. 3, 2020

(65) Prior Publication Data

US 2021/0130448 A1    May 6, 2021

Related U.S. Application Data

(60) Provisional application No. 62/929,986, filed on Nov. 4, 2019.

(51) Int. Cl.
| | |
|---|---|
| *C07K 16/28* | (2006.01) |
| *G01N 33/53* | (2006.01) |
| *C07K 16/18* | (2006.01) |
| *A61K 47/68* | (2017.01) |
| *G01N 33/68* | (2006.01) |
| *A61K 31/713* | (2006.01) |
| *G01N 33/574* | (2006.01) |
| *A61K 39/00* | (2006.01) |

(52) U.S. Cl.
CPC ............ *C07K 16/28* (2013.01); *A61K 31/713* (2013.01); *A61K 47/6803* (2017.08); *A61K 47/6843* (2017.08); *C07K 16/18* (2013.01); *G01N 33/574* (2013.01); *G01N 33/68* (2013.01); *A61K 39/001102* (2018.08); *C07K 2317/24* (2013.01)

(58) Field of Classification Search
None
See application file for complete search history.

(56) References Cited

U.S. PATENT DOCUMENTS

| | | |
|---|---|---|
| 2013/0149238 A1 | 6/2013 | Kavlie et al. |
| 2013/0303456 A1 | 11/2013 | Van Meir |
| 2014/0286936 A1 | 9/2014 | Chambers et al. |
| 2016/0297883 A1 | 10/2016 | Gallo et al. |
| 2019/0004052 A1 | 1/2019 | Herd et al. |

OTHER PUBLICATIONS

Nairet (2021). Therapeutic Application of Brain-Specific Angiogenesis Inhibitor 1 for Cancer Therapy. Cancers 13(14):2562 (13 pages).*
Tu et al., "The Adhesion-GPCR BAI1 Promotes Excitatory Synaptogenesis by Coordinating Bidirectional Trans-synaptic Signaling", The Journal of Neuroscience, 2018, 38(39), pp. 8388-8406.

* cited by examiner

*Primary Examiner* — Christine J Saoud
*Assistant Examiner* — Jon M Lockard
(74) *Attorney, Agent, or Firm* — Goodwin Procter LLP

(57) ABSTRACT

The present disclosure provides an antibody that binds human Adhesion G Protein-Coupled Receptor B1 (BAI1) protein, compositions comprising the same, and use thereof in methods of detection, methods of diagnosis, and methods of treatment.

18 Claims, 7 Drawing Sheets

Specification includes a Sequence Listing.

BRAIN-SPECIFIC ANGIOGENESIS INHIBITOR 1 (BAI1) ANTIBODIES AND USES THEREOF

REFERENCE TO SEQUENCE LISTING

This application includes a Sequence Listing filed electronically as a text file named 18909900501SEQ, created on Nov. 2, 2020, with a size of 24,971 bytes. The Sequence Listing is incorporated herein by reference.

FIELD

The present disclosure is directed to antibodies, and fragments thereof, that bind human Brain-Specific Angiogenesis Inhibitor 1 (BAI1) (also known as Adhesion G Protein-Coupled Receptor B1 (ADGRB1)) protein, compositions comprising the same, and uses thereof in methods of detection, methods of cell isolation, methods of depletion, methods of diagnosis, and methods of treatment.

BACKGROUND

BAI1 is expressed in cells of the monocyte lineage, astrocytes, neurons and Myo/Nog cells that express the skeletal muscle specific transcription factor MyoD and the bone morphogenetic inhibitor noggin. BAI1$^+$ cells are involved in innate immunity, wound healing, embryonic development, and neuroprotection. Wound healing properties of BAI1$^+$ cells reflect, in part, the role of the molecule in phagocytosing apoptotic cells and Gram-negative bacteria via its binding to phosphatidylserine. Another function of a subpopulation of BAI1$^+$ cells during wound healing is to differentiate into myofibroblasts. While myofibroblast contractions may facilitate wound closure, they also may perturb tissue morphology, and therefore function. For example, secondary cataracts or posterior capsule opacification (PCO) is a vision impairing disease of the lens that develops in some adults and most children following cataract surgery. BAI1$^+$ cells in the lens develop into myofibroblasts and produce wrinkles in the capsule, the thick basement membrane surrounding the lens. Deformations in the lens capsule affect visual acuity.

In addition to its role in phagocytosis, BAI1 is metabolized to produce an inhibitor of angiogenesis, the process whereby blood vessels develop from pre-existing vessels. In the retina, angiogenesis is a vision-threatening component of diabetic retinopathy and wet macular degeneration. Angiogenesis is also critical for the growth of tumors that cannot grow beyond a few millimeters unless they obtain an additional. BAI1$^+$ cells are present in the retina and tumors. In some cancers, BAI1 is downregulated with disease progression, thereby favoring angiogenesis. However, vascularization is also important for distribution of chemotherapy drugs, for example, those attached to viruses.

SUMMARY

The present disclosure provides antibodies, or antigen-binding fragments thereof, that bind to human BAI1 protein, wherein the antibodies, or antigen-binding fragments thereof, comprise: a first complementarity determining region (CDR) in the variable heavy ($V_H$) chain ($V_H$-CDR1) comprising or consisting of an amino acid sequence according to SEQ ID NO:7; a second CDR in the $V_H$ chain ($V_H$-CDR2) comprising or consisting of an amino acid sequence according to SEQ ID NO:8; a third CDR in the $V_H$ chain ($V_H$-CDR3) comprising or consisting of an amino acid sequence according to SEQ ID NO:9; a first CDR in the variable light ($V_L$) chain ($V_L$-CDR1) comprising or consisting of an amino acid sequence according to SEQ ID NO:10; a second CDR in the $V_L$ chain ($V_L$-CDR2) comprising or consisting of an amino acid sequence according to SEQ ID NO:11; and a third CDR in the $V_L$ chain ($V_L$-CDR3) comprising or consisting of an amino acid sequence according to SEQ ID NO:12.

The present disclosure also provides isolated nucleic acid molecules encoding the heavy chain of the antibody, or antigen-binding fragment thereof, wherein the nucleic acid molecules comprise or consist of a nucleotide sequence according to SEQ ID NO:2 or SEQ ID NO:3.

The present disclosure also provides isolated nucleic acid molecules encoding the light chain of the antibody, or antigen-binding fragment thereof, wherein the nucleic acid molecules comprise or consist of a nucleotide sequence according to SEQ ID NO:5 or SEQ ID NO:6.

The present disclosure also provides methods of detecting a cell expressing BAI1, the method comprising contacting the cell with the antibody, or antigen-binding fragment thereof, described herein and detecting the antibody, or antigen-binding fragment thereof. The detection can occur in fixed tissue, cell culture, and living animals for cell tracking and bio-imaging.

The present disclosure also provides methods of purifying BAI1, the method comprising contacting the molecule with the antibody, or antigen-binding fragment thereof, described herein. These methods include, for example, immunoprecipitation and column purification.

The present disclosure also provides methods of isolating living cells expressing BAI1, the method comprising contacting the cells with the antibody, or antigen-binding fragment thereof, and separating antibody or antigen-binding fragment bound cells from unbound cells, described herein. These methods include, for example, fluorescence activated cell sorting (FACS) and magnetic cell sorting.

The present disclosure also provides methods of analyzing BAI1 functions, the method comprising contacting molecules and living cells in vitro and in vivo with the antibody, or antigen-binding fragment thereof, described herein. These methods include, for example, blocking receptor and its fragments for enzyme linked immunosorbent assay (ELISA), immunoprecipitation, Western blotting, and live cell assays.

The present disclosure also provides methods of killing cells expressing BAI1 in vitro and in animals to determine cell functions, and in human patients in need thereof, the methods comprising administering the antibody, or antigen-binding fragment thereof, described herein.

The present disclosure also provides methods of treating a cancer expressing BAI1 in cell culture and in tumor-bearing animals and humans, the methods comprising administering the antibody, or antigen-binding fragment thereof, described herein.

The present disclosure also provides methods of treating Posterior Capsule Opacification (PCO), the methods comprising administering to tissue culture, animals and human patients in need thereof the antibody, or antigen-binding fragment thereof, described herein.

The present disclosure also provides methods of treating fibrosis, the methods comprising administering to cells in culture, animals, and human patients in need thereof the antibody, or antigen-binding fragment thereof, described herein.

The present disclosure also provides methods of promoting wound healing, the methods comprising administering to a human patient in need thereof any of the antibodies, or antigen-binding fragments thereof, described herein, or BAI1+ cells to the wound.

Figure 1:
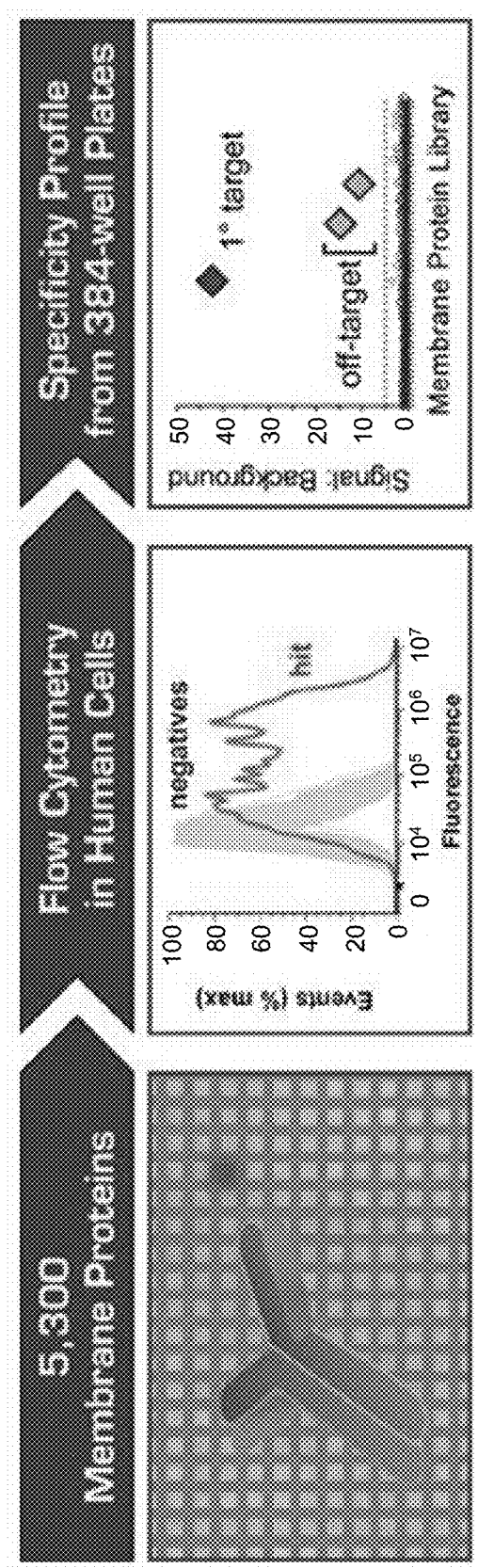
FIG. 1 shows the antigen identification workflow using the membrane proteome array (MPA) platform.

It is to be understood that both the foregoing general description and the following detailed description are exemplary and explanatory only and are not restrictive of the embodiments, as claimed herein.

DESCRIPTION OF EMBODIMENTS

The terminology used herein is for the purpose of describing particular embodiments only and is not intended to be limiting. Various terms relating to aspects of disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in any specific order. Where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, "about" means the numerical value can vary by ±10% and remain within the scope of the disclosed embodiments.

As used herein, the term "antibody" refers to an immunoglobulin molecule that specifically binds to, or is immunologically reactive with, a particular antigen, and includes polyclonal, monoclonal, genetically engineered and otherwise modified forms thereof including, but not limited to, chimeric antibodies, humanized antibodies, heteroconjugate antibodies (e.g., bispecific antibodies, diabodies, triabodies, and tetrabodies).

As used herein, the phrase "antigen-binding fragment thereof" means a fragment of an antibody that is able to bind an antigen. Antigen-binding fragments include, but are not limited to, Fab, Fab', F(ab')$_2$, Fv, scFv, scFv-Fc, diabody, bispecific diabody, trispecific triabody, minibody, monospecific Fab$_2$, bispecific Fab$_2$, trispecific Fab$_3$, nanobody, IgNAR, V-NAR, hcIgG, and VhH fragments.

As used herein, the phrase "chimeric antibody" refers to an antibody having variable sequences derived from a non-human immunoglobulin, such as rat or mouse antibody, and human immunoglobulin constant regions, typically chosen from a human immunoglobulin template.

As used herein, the term "Fv" fragment is the minimum antibody fragment that contains a complete target recognition and binding site. This region consists of a dimer of one heavy and one light chain variable domain in a noncovalent association ($V_H$-$V_L$ dimer). It is in this configuration that the three CDRs of each variable domain interact to define a target binding site on the surface of the $V_H$-$V_L$ dimer.

As used herein, the phrase "human antibodies" refers to antibodies having the amino acid sequence of a human immunoglobulin and includes antibodies isolated from human immunoglobulin libraries or from animals transgenic for one or more human immunoglobulins and that do not express endogenous immunoglobulins.

As used herein, the phrase "humanized antibody" refers to a chimeric antibody, or an antigen-binding fragment thereof, which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the framework (FR) regions that are those of a human immunoglobulin sequence. The humanized antibody can also comprise at least a portion of an immunoglobulin constant region (Fc), typically that of a human immunoglobulin consensus sequence.

As used herein, the phrase "in need thereof" means that the "subject" or "patient" has been identified as having a need for the particular method, prevention, or treatment. In some embodiments, the identification can be by any means of diagnosis. In any of the methods, preventions, and treatments described herein, the "subject" or "patient" can be in need thereof.

As used herein, a "nucleic acid molecule" is a polymeric form of nucleotides of any length, may comprise DNA and/or RNA, and can be single-stranded, double-stranded, or multiple stranded. One strand of a nucleic acid also refers to its complement.

As used herein, the phrase "primatized antibody" refers to an antibody comprising monkey variable regions and human constant regions.

As used herein, the phrase "regulatory sequence" is intended to include promoters, enhancers and other expression control elements, such as polyadenylation signals, that control the transcription or translation of the antibody chain genes.

As used herein, the term "single chain Fv" or "scFv" refers to a single chain Fv antibody in which the variable domains of the heavy chain and the light chain ($V_H$ and $V_L$ domains) from a traditional antibody have been joined to form one chain. Generally, the Fv polypeptide further comprises a polypeptide linker between the $V_H$ and $V_L$ domains which enables the scFv to form the desired structure for target binding.

As used herein, the terms "subject" and "patient" are used interchangeably. A subject includes any animal, including mammals. Mammals include, but are not limited to, farm animals (e.g., horse, cow, pig), companion animals (e.g., dog, cat), laboratory animals (e.g., mouse, rat, rabbits), and non-human primates (e.g., monkey). In some embodiments, the subject or patient is a human.

As used herein, the term "$V_H$" refers to the variable region of an immunoglobulin heavy chain of an antibody, including the heavy chain of, for example, an Fv, scFv, or Fab fragment.

As used herein, the term "$V_L$" refers to the variable region of an immunoglobulin light chain of an antibody, including the light chain of, for example, an Fv, scFv, dsFv, or Fab fragment.

The present disclosure provides antibodies, or antigen-binding fragments thereof, that bind to BAI1 protein (also known as G8 antigen). In some embodiments, the BAI1 protein comprises or consists of the amino acid sequence:

```
                                          (SEQ ID NO:15)
MRGQAAAPGPVWILAPLLLLLLLLGRRARAAAGADAGPGPEPCATLVQG

KFFGYFSAAAVFPANASRCSWTLRNPDPRRYTLYMKVAKAPVPCSGPGR

VRTYQFDSFLESTRTYLGVESFDEVLRLCDPSAPLAFLQASKQFLQMRR

QQPPQHDGLRPRAGPPGPTDDFSVEYLVVGNRNPSRAACQMLCRWLDAC

LAGSRSSHPCGIMQTPCACLGGEAGGPAAGPLAPRGDVCLRDAVAGGPE

NCLTSLTQDRGGHGATGGWKLWSLWGECTRDCGGGLQTRTRTCLPAPGV

EGGGCEGVLEEGRQCNREACGPAGRTSSRSQSLRSTDARRREELGDELQ

QFGFPAPQTGDPAAEEWSPWSVCSSTCGEGWQTRTRFCVSSSYSTQCSG

PLREQRLCNNSAVCPVHGAWDEWSPWSLCSSTCGRGFRDRTRTCRPPQF

GGNPCEGPEKQTKFCNIALCPGRAVDGNWNEWSSWSACSASCSQGRQQR

TRECNGPSYGGAECQGHWVETRDCFLQQCPVDGKWQAWASWGSCSVTCG

AGSQRRERVCSGPFFGGAACQGPQDEYRQCGTQRCPEPHEICDEDNFGA

VIWKETPAGEVAAVRCPRNATGLILRRCELDEEGIAYWEPPTYIRCVSI

DYRNIQMMTREHLAKAQRGLPGEGVSEVIQTLVEISQDGTSYSGDLLST

IDVLRNMTEIFRRAYYSPTPGDVQNFVQILSNLLAEENRDKWEEAQLAG

-continued

PNAKELFRLVEDFVDVIGFRMKDLRDAYQVTDNLVLSIHKLPASGATDI

SFPMKGWRATGDWAKVPEDRVTVSKSVFSTGLTEADEASVFVVGTVLYR

NLGSFLALQRNTTVLNSKVISVTVKPPPRSLRTPLEIEFAHMYNGTTNQ

TCILWDETDVPSSSAPPQLGPWSWRGCRTVPLDALRTRCLCDRLSTFAI

LAQLSADANMEKATLPSVTLIVGCGVSSLTLLMLVIIYVSVWRYIRSER

SVILINFCLSIISSNALILIGQTQTRNKVVCTLVAAFLHFFFLSSFCWV

LTEAWQSYMAVTGHLRNRLIRKRFLCLGWGLPALVVAISVGFTKAKGYS

TMNYCWLSLEGGLLYAFVGPAAAVVLVNMVIGILVFNKLVSKDGITDKK

LKERAGASLWSSCVVLPLLALTWMSAVLAVTDRRSALFQILFAVFDSLE

GFVIVMVHCILRREVQDAVKCRVVDRQEEGNGDSGGSFQNGHAQLMTDF

EKDVDLACRSVLNKDIAACRTATITGTLKRPSLPEEEKLKLAHAKGPPT

NFNSLPANVSKLHLHGSPRYPGGPLPDFPNHSLTLKRDKAPKSSFVGDG

DIFKKLDSELSRAQEKALDTSYVILPTATATLRPKPKEEPKYSIHIDQM

PQTRLIHLSTAPEASLPARSPPSRQPPSGGPPEAPPAQPPPPPPPPPPP

PQQPLPPPPNLEPAPPSLGDPGEPAAHPGPSTGPSTKNENVATLSVSSL

ERRKSRYAELDFEKIMHTRKRHQDMFQDLNRKLQHAAEKDKEVLGPDSK

PEKQQTPNKRPWESLRKAHGTPTWVKKELEPLQPSPLELRSVEWERSGA

TIPLVGQDIIDLQTEV.
```

In some embodiments, the antibodies, or antigen-binding fragments thereof, described herein bind to an epitope within the human BAI1 protein comprising or consisting of the amino acids: Y83, F135, W415, W418, L420, T424, R432, R434, I458, W473, W476, R545, Y639, and L776. In some embodiments, the epitope within the human BAI1 protein to which the antibodies, or antigen-binding fragments thereof, described herein bind comprise or consist of at least 4 to 14, at least 4 to 13, at least 4 to 12, at least 4 to 11, at least 4 to 10, at least 4 to 9, at least 4 to 8, at least 4 to 7, or at least 4 to 6 of these amino acids. In some embodiments, the epitope within the human BAI1 protein to which the antibodies, or antigen-binding fragments thereof, described herein bind comprise or consist of at least 6 to 14, at least 6 to 13, at least 6 to 12, at least 6 to 11, at least 6 to 10, at least 6 to 9, or at least 6 to 8 of these amino acids. In some embodiments, the epitope within the human BAI1 protein to which the antibodies, or antigen-binding fragments thereof, described herein bind comprise or consist of at least 7 to 14, at least 7 to 13, at least 7 to 12, at least 7 to 11, at least 7 to 10, or at least 7 to 9 of these amino acids. In some embodiments, the antibodies, or antigen-binding fragments thereof, described herein bind to an epitope within the human BAI1 protein comprising or consisting of the amino acids: F135, W415, W418, L420, T424, R432, R434, and I458. In some embodiments, the antibodies, or antigen-binding fragments thereof, described herein bind to an epitope within the human BAI1 protein comprising or consisting of the amino acids: W415, W418, L420, T424, R432, R434, and I458. In some embodiments, the antibodies, or antigen-binding fragments thereof, described herein bind to an epitope within the human BAI1 protein comprising or consisting of the amino acids: T424, R432, R434, and I458.

The present disclosure also provides antibodies, or antigen-binding fragments thereof, that bind to human BAI1 protein. In some embodiments, the antibodies, or antigen-binding fragments thereof, comprise three $V_H$ CDRs and three $V_L$ CDRs.

In some embodiments, the antibodies, or antigen-binding fragments thereof, comprise a first CDR in the $V_H$ chain ($V_H$-CDR1) comprising or consisting of the amino acid sequence GYSITSDY (SEQ ID NO:7). In some embodiments, this $V_H$-CDR1 can comprise or consist of one, two, or three conservative amino acid substitutions.

In some embodiments, the antibodies, or antigen-binding fragments thereof, comprise a second CDR in the $V_H$ chain ($V_H$-CDR2) comprising or consisting of the amino acid sequence SYSGS (SEQ ID NO:8). In some embodiments, this $V_H$-CDR2 can comprise or consist of one or two conservative amino acid substitutions.

In some embodiments, the antibodies, or antigen-binding fragments thereof, comprise a third CDR in the $V_H$ chain ($V_H$-CDR3) comprising or consisting of the amino acid sequence AQGYAMDY (SEQ ID NO:9). In some embodiments, this $V_H$-CDR3 can comprise or consist of one, two, or three conservative amino acid substitutions.

In some embodiments, the antibodies, or antigen-binding fragments thereof, comprise a first CDR in the $V_L$ chain ($V_L$-CDR1) comprising or consisting of the amino acid sequence RASQSISDYLH (SEQ ID NO:10). In some embodiments, this $V_L$-CDR1 can comprise or consist of one, two, three, or four conservative amino acid substitutions.

In some embodiments, the antibodies, or antigen-binding fragments thereof, comprise a second CDR in the $V_L$ chain ($V_L$-CDR2) comprising or consisting of the amino acid sequence YASQSIS (SEQ ID NO:11). In some embodiments, this $V_L$-CDR2 can comprise or consist of one or two conservative amino acid substitutions.

In some embodiments, the antibodies, or antigen-binding fragments thereof, comprise a third CDR in the $V_L$ chain ($V_L$-CDR3) comprising or consisting of the amino acid sequence QNGHSFPFT (SEQ ID NO:12). In some embodiments, this $V_L$-CDR3 can comprise or consist of one, two, or three conservative amino acid substitutions.

In some embodiments, the antibodies, or antigen-binding fragments thereof, comprise: a first CDR in the $V_H$ chain ($V_H$-CDR1) comprising or consisting of the amino acid sequence GYSITSDY (SEQ ID NO:7), a second CDR in the $V_H$ chain ($V_H$-CDR2) comprising or consisting of the amino acid sequence SYSGS (SEQ ID NO:8), a third CDR in the $V_H$ chain ($V_H$-CDR3) comprising or consisting of the amino acid sequence AQGYAMDY (SEQ ID NO:9), a first CDR in the $V_L$ chain ($V_L$-CDR1) comprising or consisting of the amino acid sequence RASQSISDYLH (SEQ ID NO:10), a second CDR in the $V_L$ chain ($V_L$-CDR2) comprising or consisting of the amino acid sequence YASQSIS (SEQ ID NO:11), and a third CDR in the $V_L$ chain ($V_L$-CDR3) comprising or consisting of the amino acid sequence QNGHSFPFT (SEQ ID NO:12). In some embodiments, the CDRs can have the conservative amino acid substitutions described herein.

In some embodiments, the antibodies, or antigen-binding fragments thereof, comprise a $V_H$ chain comprising or consisting of the amino acid sequence:

```
                                              (SEQ ID NO:1)
SDVQLQESGPGLVKPSQSLSLTCTVTGYSITSDYAWNWIRQFPGNKLEW

MGYISYSGSTSYNPSLKSRISITRDTSKNQFFLQLNSVTTEDTATYYCA

NAQGYAMDYWGQGTSVTVSS.
```

In some embodiments, the antibodies, or antigen-binding fragments thereof, comprise a $V_H$ chain consisting of the amino acid sequence according to SEQ ID NO:1.

In some embodiments, the antibodies, or antigen-binding fragments thereof, comprise a $V_H$ chain comprising or consisting of an amino acid sequence having at least about 85%, at least about 90%, at least about 92%, at least about 94%, at least about 96%, or at least about 98% sequence identity to SEQ ID NO:1. In some embodiments, the antibodies, or antigen-binding fragments thereof, comprise a $V_H$ chain comprising or consisting of an amino acid sequence having at least about 85% sequence identity to SEQ ID NO:1. In some embodiments, the antibodies, or antigen-binding fragments thereof, comprise a $V_H$ chain comprising or consisting of an amino acid sequence having at least about 90% sequence identity to SEQ ID NO:1. In some embodiments, the antibodies, or antigen-binding fragments thereof, comprise a $V_H$ chain comprising or consisting of an amino acid sequence having at least about 92% sequence identity to SEQ ID NO:1. In some embodiments, the antibodies, or antigen-binding fragments thereof, comprise a $V_H$ chain comprising or consisting of an amino acid sequence having at least about 94% sequence identity to SEQ ID NO:1. In some embodiments, the antibodies, or antigen-binding fragments thereof, comprise a $V_H$ chain comprising or consisting of an amino acid sequence having at least about 96% sequence identity to SEQ ID NO:1. In some embodiments, the antibodies, or antigen-binding fragments thereof, comprise a $V_H$ chain comprising or consisting of an amino acid sequence having at least about 98% sequence identity to SEQ ID NO:1. In some embodiments, the $V_H$ chain comprises any of the $V_H$ CDRs described herein. In some embodiments, the $V_H$ CDRs comprise the amino acid sequences according to SEQ ID NO:7, SEQ ID NO:8, and SEQ ID NO:9. In some embodiments, the $V_H$ chain comprises or consists of one, two, three, four, five, six, seven, or eight conservative amino acid substitutions. In some embodiments, the $V_H$ chain comprises or consists of one, two, three, four, five, six, seven, or eight conservative amino acid substitutions outside of the CDRs.

In some embodiments, the antibodies, or antigen-binding fragments thereof, comprise a $V_L$ chain comprising or consisting of the amino acid sequence:

```
                                              (SEQ ID NO:4)
DIVMTQSPAGSDFTLSINSVEPEDVGVYYCQNGHSFPFTFGSGTKLEIK

TLSVTPGDRVSLSCRASQSISDYLHWYQQKSHESPRLLIKYASQSISGI

PSRFSGSGS.
```

In some embodiments, the antibodies, or antigen-binding fragments thereof, comprise a $V_L$ chain consisting of the amino acid sequence according to SEQ ID NO:4.

In some embodiments, the antibodies, or antigen-binding fragments thereof, comprise a $V_L$ chain comprising or consisting of an amino acid sequence having at least about 85%, at least about 90%, at least about 92%, at least about 94%, at least about 96%, or at least about 98% sequence identity to SEQ ID NO:4. In some embodiments, the antibodies, or antigen-binding fragments thereof, comprise a $V_L$ chain comprising or consisting of an amino acid sequence having at least about 85% sequence identity to SEQ ID NO:4. In some embodiments, the antibodies, or antigen-binding fragments thereof, comprise a $V_L$ chain comprising or consisting of an amino acid sequence having at least about 90% sequence identity to SEQ ID NO:4. In some embodiments, the antibodies, or antigen-binding fragments thereof, comprise a $V_L$ chain comprising or consisting of an amino acid sequence having at least about 92% sequence identity to SEQ ID NO:4. In some embodiments, the antibodies, or antigen-binding fragments thereof, comprise a $V_L$ chain comprising or consisting of an amino acid sequence having at least about 94% sequence identity to SEQ ID NO:4. In some embodiments, the antibodies, or antigen-binding fragments thereof, comprise a $V_L$ chain comprising or consisting of an amino acid sequence having at least about 96% sequence identity to SEQ ID NO:4. In some embodiments, the antibodies, or antigen-binding fragments thereof, comprise a $V_L$ chain comprising or consisting of an amino acid sequence having at least about 98% sequence identity to SEQ ID NO:4. In some embodiments, the $V_L$ chain comprises any of the $V_L$ CDRs described herein. In some embodiments, the $V_L$ CDRs comprise the amino acid sequences according to SEQ ID NO:10, SEQ ID NO:11, and SEQ ID NO:12. In some embodiments, the $V_L$ chain comprises one, two, three, four, five, six, seven, or eight conservative amino acid substitutions. In some embodiments, the $V_L$ chain comprises one, two, three, four, five, six, seven, or eight conservative amino acid substitutions outside of the CDRs.

In some embodiments, the antibodies, or antigen-binding fragments thereof, comprise a $V_H$ chain comprising the amino acid sequence according to SEQ ID NO:1 and a $V_L$ chain comprising the amino acid sequence according to SEQ ID NO:4. In some embodiments, the antibodies, or antigen-binding fragments thereof, comprise a $V_H$ chain consisting of the amino acid sequence according to SEQ ID NO:1 and a $V_L$ chain consisting of the amino acid sequence according to SEQ ID NO:4.

In some embodiments, the antibodies, or antigen-binding fragments thereof, comprise a $V_H$ chain and a $V_L$ chain comprising or consisting of an amino acid sequence having at least about 85%, at least about 90%, at least about 92%, at least about 94%, at least about 96%, or at least about 98% sequence identity to SEQ ID NO:1 and SEQ ID NO:4, respectively. In some embodiments, the antibodies, or antigen-binding fragments thereof, comprise a $V_H$ chain and a $V_L$ chain comprising or consisting of an amino acid sequence having at least about 85% sequence identity to SEQ ID NO:1 and SEQ ID NO:4, respectively. In some embodiments, the antibodies, or antigen-binding fragments thereof, comprise a $V_H$ chain and a $V_L$ chain comprising or consisting of an amino acid sequence having at least about 90% sequence identity to SEQ ID NO:1 and SEQ ID NO:4, respectively. In some embodiments, the antibodies, or antigen-binding fragments thereof, comprise a $V_H$ chain and a $V_L$ chain comprising or consisting of an amino acid sequence having at least about 92% sequence identity to SEQ ID NO:1 and SEQ ID NO:4, respectively. In some embodiments, the antibodies, or antigen-binding fragments thereof, comprise a $V_H$ chain and a $V_L$ chain comprising or consisting of an amino acid sequence having at least about 94% sequence identity to SEQ ID NO:1 and SEQ ID NO:4, respectively. In some embodiments, the antibodies, or antigen-binding fragments thereof, comprise a $V_H$ chain and a $V_L$ chain comprising or consisting of an amino acid sequence having at least about 96% sequence identity to SEQ ID NO:1 and SEQ ID NO:4, respectively. In some embodiments, the antibodies, or antigen-binding fragments thereof, comprise a $V_H$ chain and a $V_L$ chain comprising or consisting of an amino acid sequence having at least about 98% sequence identity to SEQ ID NO:1 and SEQ ID NO:4, respectively. In some embodiments, the $V_H$ chain and the $V_L$ chain comprise any of the $V_H$ CDRs and $V_L$ CDRs described herein. In some embodiments, the $V_H$ CDRs comprise the amino acid sequences according to SEQ ID NO:7, SEQ ID NO:8, and SEQ ID NO:9. In some embodiments, the $V_L$ CDRs comprise or consist of the amino acid sequences according to SEQ ID NO:10, SEQ ID NO:11, and SEQ ID NO:12. In some embodiments, the $V_H$ chain and the $V_L$ chain each can comprise or consist of one, two, three, four, five, six, seven, or eight conservative amino acid substitutions. In some embodiments, the $V_H$ chain and the $V_L$ chain each can comprise or consist of one, two, three, four, five, six, seven, or eight conservative amino acid substitutions outside of the CDRs.

The antibodies, or antigen-binding fragments thereof, can be any isotype. In some embodiments, the antibody is an IgM or IgG antibody. In some embodiments, the antibody is an IgM antibody. In some embodiments, the antibody is an IgG antibody. In some embodiments, the antibody is an IgG1 antibody. In some embodiments, the IgG1 antibody is an IgG1 G1m1, G1m2, G1m3, G1m17, nG1m1, nG1m2, or nG1m17 allotype antibody. In some embodiments, the antibody is an IgG1 G1m17 allotype antibody.

In some embodiments, the variant IgG1 heavy chain is paired with a kappa light chain of allotype Km1, Km2, or Km3. In some embodiments, the variant IgG1 heavy chain is paired with a lambda light chain.

In some embodiments, the antibodies, or antigen-binding fragments thereof, are humanized and IgG. In some embodiments, the antibodies, or antigen-binding fragments thereof, are humanized and IgG1.

In some embodiments, the antibody, or antigen-binding fragment thereof, is a chimeric antibody, or antigen-binding fragment thereof. Methods for producing chimeric antibodies are known in the art (see, Morrison, Science, 1985, 229, 1202-1207; Oi et al., BioTechniques, 1986, 4, 214-221; Gillies et al., J. Immunol. Methods, 1985, 125, 191-202; and U.S. Pat. Nos. 5,807,715, 4,816,567, and 4,816,397).

In some embodiments, the chimeric antibody, or antigen-binding fragment thereof, is a primatized chimeric antibody, or antigen-binding fragment thereof. Methods for producing primatized antibodies are known in the art (see, U.S. Pat. Nos. 5,658,570, 5,681,722, and 5,693,780).

In some embodiments, the chimeric antibody, or antigen-binding fragment thereof, is a humanized antibody, or antigen-binding fragment thereof. Methods for producing humanized antibodies are known in the art (see, Riechmann et al., Nature, 1988, 332, 323-327; Padlan, Mol. Immunol., 1991, 28, 489-498; Studnicka et al., Prot. Eng., 1994, 7, 805-814; Roguska et al., Proc. Natl. Acad. Sci., 1994, 91, 969-973; European Patent Nos. EP239400, EP592106, and EP519596; PCT Publication WO 91/09967; and U.S. Pat. Nos. 5,225,539, 5,530,101, 5,585,089, 5,693,761, 5,693, 762, 6,180,370, and 5,565,332).

In some embodiments, the humanized antibodies, or antigen-binding fragments thereof, comprise a heavy chain comprising or consisting of the amino acid sequence:

```
                                           (SEQ ID NO:13)
VQLQESGPGLVKPSQSLSLTCTVTGYSITSDYAWNWIRQFPGNKLEWMG

YISYSGSTSYNPSLKSRISITRDTSKNQFFLQLNSVTTEDTATYYCANA

QGYAMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK
```

-continued

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLS

LSPG.

In some embodiments, the humanized antibodies, or antigen-binding fragments thereof, comprise a heavy chain consisting of the amino acid sequence according to SEQ ID NO:13.

In some embodiments, the humanized antibodies, or antigen-binding fragments thereof, comprise a heavy chain comprising or consisting of an amino acid sequence having at least about 85%, at least about 90%, at least about 92%, at least about 94%, at least about 96%, or at least about 98% sequence identity to SEQ ID NO:13. In some embodiments, the humanized antibodies, or antigen-binding fragments thereof, comprise a heavy chain comprising or consisting of an amino acid sequence having at least about 85% sequence identity to SEQ ID NO:13. In some embodiments, the humanized antibodies, or antigen-binding fragments thereof, comprise a heavy chain comprising or consisting of an amino acid sequence having at least about 90% sequence identity to SEQ ID NO:13. In some embodiments, the humanized antibodies, or antigen-binding fragments thereof, comprise a heavy chain comprising or consisting of an amino acid sequence having at least about 92% sequence identity to SEQ ID NO:13. In some embodiments, the humanized antibodies, or antigen-binding fragments thereof, comprise a heavy chain comprising or consisting of an amino acid sequence having at least about 94% sequence identity to SEQ ID NO:13. In some embodiments, the humanized antibodies, or antigen-binding fragments thereof, comprise a heavy chain comprising or consisting of an amino acid sequence having at least about 96% sequence identity to SEQ ID NO:13. In some embodiments, the humanized antibodies, or antigen-binding fragments thereof, comprise a heavy chain comprising or consisting of an amino acid sequence having at least about 98% sequence identity to SEQ ID NO:13. In some embodiments, the heavy chain comprises any of the $V_H$ CDRs described herein. In some embodiments, the heavy chain CDRs comprise the amino acid sequences according to SEQ ID NO:7, SEQ ID NO:8, and SEQ ID NO:9. In some embodiments, the heavy chain comprises one, two, three, four, five, six, seven, eight, nine, or ten conservative amino acid substitutions. In some embodiments, the heavy chain comprises one, two, three, four, five, six, seven, eight, nine, or ten conservative amino acid substitutions outside of the CDRs.

In some embodiments, the humanized antibodies, or antigen-binding fragments thereof, comprise a light chain comprising or consisting of the amino acid sequence:

(SEQ ID NO:14)
DIVMTQSPATLSVTPGDRVSLSCRASQSISDYLHWYQQKSHESPRLLIK

YASQSISGIPSRFSGSGSGSDFTLSINSVEPEDVGVYYCQNGHSFPFTF

GSGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

In some embodiments, the humanized antibodies, or antigen-binding fragments thereof, comprise a light chain consisting of the amino acid sequence according to SEQ ID NO:14.

In some embodiments, the humanized antibodies, or antigen-binding fragments thereof, comprise a light chain comprising or consisting of an amino acid sequence having at least about 85%, at least about 90%, at least about 92%, at least about 94%, at least about 96%, or at least about 98% sequence identity to SEQ ID NO:14. In some embodiments, the humanized antibodies, or antigen-binding fragments thereof, comprise a light chain comprising or consisting of an amino acid sequence having at least about 85% sequence identity to SEQ ID NO:14. In some embodiments, the humanized antibodies, or antigen-binding fragments thereof, comprise a light chain comprising or consisting of an amino acid sequence having at least about 90% sequence identity to SEQ ID NO:14. In some embodiments, the humanized antibodies, or antigen-binding fragments thereof, comprise a light chain comprising or consisting of an amino acid sequence having at least about 92% sequence identity to SEQ ID NO:14. In some embodiments, the humanized antibodies, or antigen-binding fragments thereof, comprise a light chain comprising or consisting of an amino acid sequence having at least about 94% sequence identity to SEQ ID NO:14. In some embodiments, the humanized antibodies, or antigen-binding fragments thereof, comprise a light chain comprising or consisting of an amino acid sequence having at least about 96% sequence identity to SEQ ID NO:14. In some embodiments, the humanized antibodies, or antigen-binding fragments thereof, comprise a light chain comprising or consisting of an amino acid sequence having at least about 98% sequence identity to SEQ ID NO:14. In some embodiments, the light chain comprises any of the $V_L$ CDRs described herein. In some embodiments, the light chain CDRs comprise the amino acid sequences according to SEQ ID NO:10, SEQ ID NO:11, and SEQ ID NO:12. In some embodiments, the light chain comprises or consists of one, two, three, four, five, six, seven, eight, nine, or ten conservative amino acid substitutions. In some embodiments, the light chain comprises or consists of one, two, three, four, five, six, seven, eight, nine, or ten conservative amino acid substitutions outside of the CDRs.

In some embodiments, the humanized antibodies, or antigen-binding fragments thereof, comprise a heavy chain and a light chain comprising or consisting of an amino acid sequence having at least about 85%, at least about 90%, at least about 92%, at least about 94%, at least about 96%, or at least about 98% sequence identity to SEQ ID NO:13 and SEQ ID NO:14, respectively. In some embodiments, the humanized antibodies, or antigen-binding fragments thereof, comprise a heavy chain and a light chain comprising or consisting of an amino acid sequence having at least about 85% sequence identity to SEQ ID NO:13 and SEQ ID NO:14, respectively. In some embodiments, the humanized antibodies, or antigen-binding fragments thereof, comprise a heavy chain and a light chain comprising or consisting of an amino acid sequence having at least about 90% sequence identity to SEQ ID NO:13 and SEQ ID NO:14, respectively. In some embodiments, the humanized antibodies, or antigen-binding fragments thereof, comprise a heavy chain and a light chain comprising or consisting of an amino acid sequence having at least about 92% sequence identity to SEQ ID NO:13 and SEQ ID NO:14, respectively. In some embodiments, the humanized antibodies, or antigen-binding fragments thereof, comprise a heavy chain and a light chain comprising or consisting of an amino acid sequence having at least about 94% sequence identity to SEQ ID NO:13 and SEQ ID NO:14, respectively. In some embodiments, the humanized antibodies, or antigen-binding fragments thereof, comprise a heavy chain and a light chain comprising or consisting of an amino acid sequence having at least about 96% sequence identity to SEQ ID NO:13 and SEQ ID NO:14, respectively. In some embodiments, the humanized antibodies, or antigen-binding fragments thereof, comprise a heavy chain and a light chain comprising or consisting of an amino acid sequence having at least about 98% sequence identity to SEQ ID NO:13 and SEQ ID NO:14, respectively. In some embodiments, the heavy chain and light chain comprise any of the $V_H$ CDRs and $V_L$ CDRs described herein. In some embodiments, the $V_H$ CDRs comprise the amino acid sequences according to SEQ ID NO:7, SEQ ID NO:8, and SEQ ID NO:9. In some embodiments, the $V_L$ CDRs comprise or consist of the amino acid sequences according to SEQ ID NO:10, SEQ ID NO:11, and SEQ ID NO:12. In some embodiments, the heavy chain and light chain each can comprise or consist of one, two, three, four, five, six, seven, eight, nine, or ten conservative amino acid substitutions. In some embodiments, the heavy chain and light chain each can comprise or consist of one, two, three, four, five, six, seven, eight, nine, or ten conservative amino acid substitutions outside of the CDRs.

In some embodiments, the antibody, or antigen-binding fragment thereof, is completely humanized. Completely "human" antibodies can be desirable for therapeutic treatment of human patients. Methods for producing completely human antibodies are known in the art, including phage display methods using antibody libraries derived from human immunoglobulin sequences (see, U.S. Pat. Nos. 4,444,887 and 4,716,111; and PCT Publications WO 98/46645, WO 98/50433, WO 98/24893, WO 98/16654, WO 96/34096, WO 96/33735, and WO 91/10741). Human antibodies can also be produced using transgenic mice which are incapable of expressing functional endogenous immunoglobulins, but which can express human immunoglobulin genes (see, PCT Publications WO 98/24893, WO 92/01047, WO 96/34096, and WO 96/33735; and U.S. Pat. Nos. 5,413,923, 5,625,126, 5,633,425, 5,569,825, 5,661, 016, 5,545,806, 5,814,318, 5,885,793, 5,916,771, and 5,939, 598). Completely human antibodies that recognize a selected epitope can also be generated using a technique referred to as "guided selection" (see, Jespers et al., Biotechnology, 1988, 12, 899-903).

In some embodiments, the antibodies, or antigen-binding fragments thereof, are bispecific antibodies. Bispecific antibodies have binding specificities for at least two different antigens (i.e., one of the binding specificities is directed to BAI1, and the other binding specificity is for any other antigen, such as a cell-surface protein, receptor, receptor subunit, tissue-specific antigen, virally derived protein, virally encoded envelope protein, bacterially derived protein, or bacterial surface protein, etc.).

In some embodiments, the antibodies, or antigen-binding fragments thereof, are derivatized antibodies. For example, the derivatized antibodies can be antibodies modified by glycosylation, acetylation, pegylation, phosphorylation, amidation, derivatization by known protecting/blocking groups, proteolytic cleavage, linkage to a cellular ligand or other protein, and the like. Any of numerous chemical modifications can be carried out by known techniques, including, but not limited to, specific chemical cleavage, acetylation, formylation, metabolic synthesis of tunicamycin, and the like. In addition, the derivative can contain one or more non-natural amino acids, such as using ambrx technology (see, Wolfson, Chem. Biol., 2006, 13, 1011-1012).

In some embodiments, the antibodies, or antigen-binding fragments thereof, are derivatized through glycosylation. Suitable biantennary complexes can be composed of a core structure having two N-acetylglucosamine (GlcNAc), three mannose, and two GlcNAc residues that are β-1,2 linked to α-6 mannose and α-3 mannose to form two antennae. One or more fucose (Fuc), galactose (Gal), high mannose glycans Man-5 or Man-9, bisecting GlcNAc, and sialic acid including N-acetylneuraminic acid (NANA) or N-glycolylneuraminic acid (NGNA) residues may be attached to the core. N-linked glycoforms may include G0 (protein having a core biantennary glycosylation structure), G0F (fucosylated G0), G0F GlcNAc, G1 (protein having a core glycosylation structure with one galactose residue), G1F (fucosylated G1), G2 (protein having a core glycosylation structure with two galactose residues), and/or G2F (fucosylated G2). In some embodiments, an anti-BAI1 antibody has a G0F glycan.

The antibodies, or antigen-binding fragments thereof, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies can be used to obtain antibody heavy and light chain genes, incorporate these genes into recombinant expression vectors and introduce the vectors into host cells (see, Molecular Cloning; A Laboratory Manual, Second Edition, Sambrook, Fritsch and Maniatis (eds.), Cold Spring Harbor, N.Y., 1989; Current Protocols in Molecular Biology, Ausubel et al., eds., Greene Publishing Associates, 1989; and U.S. Pat. No. 4,816,397).

In some embodiments, to generate nucleic acid molecules encoding the antibodies, or antigen-binding fragments thereof, described herein, DNA fragments encoding the light and heavy chain variable regions are first obtained. These DNAs can be obtained by amplification and modification of germline DNA or cDNA encoding light and heavy chain variable sequences, for example, using the polymerase chain reaction (PCR). Germline DNA sequences for human heavy and light chain variable region genes are known in the art (see, the "VBASE" human germline sequence database; Kabat et al., 1991, Sequences of Proteins of Immunological Interest, Fifth Edition, U.S. Department of Health and Human Services, NIH Publication No. 91-3242; Tomlinson et al., J. Mol. Biol., 1992, 22T, 116-198; and Cox et al., Eur. J. Immunol., 1994, 24, 827-836). A DNA fragment encoding the heavy or light chain variable region can be synthesized and used as a template for mutagenesis to generate a variant as described herein using routine mutagenesis techniques; alternatively, a DNA fragment encoding the variant can be directly synthesized.

The present disclosure provides isolated nucleic acid molecules encoding the $V_H$ chain of the antibody, or antigen-binding fragment thereof, wherein the nucleic acid molecule comprises or consists of the nucleotide sequence:

(SEQ ID NO:2; DNA)
TCTGATGTGCAGCTTCAGGAGTCGGGACCTGGCCTGGTGAAACCTTCTC

AGTCTCTGTCCCTCACCTGCACTGTCACTGGCTACTCAATCACCAGTGA

TTATGCCTGGAACTGGATCCGGCAGTTTCCAGGAAACAAACTGGAGTGG

ATGGGCTACATAAGCTACAGTGGTAGCACTAGCTACAACCCATCTCTCA

AAAGTCGAATCTCTATCACTCGAGACACATCCAAGAACCAGTTCTTCCT

GCAGTTGAATTCTGTGACTACTGAGGACACAGCCACATATTACTGTGCC

AATGCCCAGGGGTATGCTATGGACTACTGGGGTCAAGGAACCTCAGTCA

CCGTCTCCTCA or (SEQ ID NO:3; RNA)
UCUGAUGUGCAGCUUCAGGAGUCGGGACCUGGCCUGGUGAAACCUUCUC

AGUCUCUGUCCCUCACCUGCACUGUCACUGGCUACUCAAUCACCAGUGA

UUAUGCCUGGAACUGGAUCCGGCAGUUUCCAGGAAACAAACUGGAGUGG

AUGGGCUACAUAAGCUACAGUGGUAGCACUAGCUACAACCCAUCUCUCA

AAAGUCGAAUCUCUAUCACUCGAGACACAUCCAAGAACCAGUUCUUCCU

GCAGUUGAAUUCUGUGACUACUGAGGACACAGCCACAUAUUACUGUGCC

AAUGCCCAGGGGUAUGCUAUGGACUACUGGGGUCAAGGAACCUCAGUCA

CCGUCUCCUCA.

The present disclosure also provides isolated nucleic acid molecules encoding the $V_L$ chain of the antibody, or antigen-binding fragment thereof, wherein the nucleic acid molecule comprises or consists of the nucleotide sequence:

(SEQ ID NO:5, DNA)
GACATTGTGATGACTCAGTCTCCAGCCACCCTGTCTGTGACTCCAGGAG

ATAGAGTCTCTCTTTCCTGCAGGGCCAGCCAGAGTATTAGCGACTACTT

ACACTGGTATCAACAAAAATCACATGAGTCTCCAAGGCTTCTCATCAAA

TATGCTTCCCAATCCATCTCTGGGATCCCCTCCAGGTTCAGTGGCAGTG

GATCAGGGTCAGATTTCACTCTCAGTATCAACAGTGTGGAACCTGAAGA

TGTTGGAGTGTATTACTGTCAAAATGGTCACAGCTTTCCATTCACGTTC

GGCTCGGGGACAAAGTTGGAAATAAAA or (SEQ ID NO:6, RNA)
GACAUUGUGAUGACUCAGUCUCCAGCCACCCUGUCUGUGACUCCAGGAG

AUAGAGUCUCUCUUUCCUGCAGGGCCAGCCAGAGUAUUAGCGACUACUU

ACACUGGUAUCAACAAAAAUCACAUGAGUCUCCAAGGCUUCUCAUCAAA

UAUGCUUCCCAAUCCAUCUCUGGGAUCCCCUCCAGGUUCAGUGGCAGUG

GAUCAGGGUCAGAUUUCACUCUCAGUAUCAACAGUGUGGAACCUGAAGA

UGUUGGAGUGUAUUACUGUCAAAAUGGUCACAGCUUUCCAUUCACGUUC

GGCUCGGGGACAAAGUUGGAAAUAAAA.

These DNA fragments can be further manipulated by standard recombinant DNA techniques, for example, to convert the variable region genes to full-length antibody chain genes, to Fab fragment genes or to a scFv gene. In these manipulations, a $V_H$- or $V_L$-encoding DNA fragment is operatively linked to another DNA fragment encoding another protein, such as an antibody constant region or a flexible linker. The phrase "operatively linked," as used in this context, is intended to mean that the two DNA fragments are joined such that the amino acid sequences encoded by the two DNA fragments remain in-frame.

The isolated DNA molecules encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (see, Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region. In some embodiments, the heavy chain constant region is an $IgG_1$ or $IgG_4$ constant region. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see, Kabat et al., 1991, Sequences of Proteins of Immunological Interest, Fifth Edition (U.S. Department of Health and Human Services, NIH Publication No. 91-3242)) and DNA fragments encompassing these regions can be obtained by standard PCR amplification. The light chain constant region can be a kappa or lambda constant region. In some embodiments, the light chain constant region is a kappa constant region. To create an scFv gene, the $V_H$- and $V_L$-encoding DNA fragments are operatively linked to another fragment encoding a flexible linker, for example, encoding the amino acid sequence $(Gly_4Ser)_3$, such that the $V_H$ and $V_L$ sequences can be expressed as a contiguous single-chain protein, with the $V_L$ and $V_H$ regions joined by the flexible linker (see, Bird et al., Science, 1988, 242, 423-426; Huston et al., Proc. Natl. Acad. Sci. USA, 1988, 85, 5879-5883; and McCafferty et al., Nature, 1990, 348, 552-554).

To express the antibodies, or antigen-binding fragments thereof, described herein, DNA molecules encoding partial or full-length light and heavy chains, obtained as described herein, can be inserted into expression vectors such that the genes are operatively linked to transcriptional and translational control sequences. In this context, the phrase "operatively linked" is intended to mean that an antibody gene is ligated into a vector such that transcriptional and translational control sequences within the vector serve their intended function of regulating the transcription and translation of the antibody gene. The expression vector and expression control sequences can be chosen to be compatible with the expression host cell used. The antibody light chain gene and the antibody heavy chain gene can be inserted into separate vectors or, more typically, both genes are inserted into the same expression vector.

The antibody genes can be inserted into the expression vector by standard methods such as, for example, ligation of complementary restriction sites on the antibody gene fragment and vector, or blunt end ligation if no restriction sites are present. Prior to insertion of the light or heavy chain sequences, the expression vector can already carry antibody constant region sequences. For example, one approach to converting the $V_H$ and $V_L$ sequences to full-length antibody genes is to insert them into expression vectors already encoding heavy chain constant and light chain constant regions, respectively, such that the $V_H$ segment is operatively linked to the $C_H$ segment(s) within the vector and the $V_L$ segment is operatively linked to the $C_L$ segment within the vector. Additionally or alternately, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide, such as a signal peptide from a non-immunoglobulin protein.

In addition to the antibody chain genes, the recombinant expression vectors can carry regulatory sequences that control the expression of the antibody chain genes in a host cell. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, and the like. Suitable regulatory sequences for mammalian host cell expression include viral sequences that direct high levels of protein expression in mammalian cells, such as promoters and/or enhancers derived from cytomegalovirus (CMV) (such as the CMV promoter/enhancer), Simian Virus (SV40) (such as the SV40 promoter/enhancer), adenovirus, (such as the adenovirus major late promoter (AdMLP)) and polyoma. Viral regulatory elements and sequences thereof are known in the art (see, e.g., U.S. Pat. Nos. 5,168,062, 4,510,245, and 4,968,615).

The recombinant expression vectors of the disclosure can also carry additional sequences, such as sequences that regulate replication of the vector in host cells (such as origins of replication) and selectable marker genes. The selectable marker gene facilitates selection of host cells into which the vector has been introduced (see, U.S. Pat. Nos. 4,399,216, 4,634,665, and 5,179,017). For example, typically the selectable marker gene confers resistance to drugs, such as G418, puromycin, blasticidin, hygromycin, or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, such as electroporation, lipofection, calcium-phosphate precipitation, DEAE-dextran transfection, and the like.

The antibodies, or antigen-binding fragments thereof, can be expressed in either prokaryotic or eukaryotic host cells. In some embodiments, expression of antibodies, or antigen-binding fragments thereof, can be performed in eukaryotic cells, such as mammalian host cells, for secretion of a properly folded and immunologically active antibody. Exemplary mammalian host cells for expressing the recombinant antibodies, or antigen-binding fragments thereof, of the disclosure include Chinese Hamster Ovary (CHO cells) (including DHFR CHO cells (see, Urlaub, Proc. Natl. Acad. Sci. USA, 1980, 77, 4216-4220), used with a DHFR selectable marker (see, Kaufman, Mol. Biol., 1982, 159, 601-621), NS0 myeloma cells, COS cells, 293 cells, and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies, or antigen-binding fragments thereof, can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of antibodies, or antigen-binding fragments thereof, described herein.

Recombinant DNA technology can also be used to remove some or all of the DNA encoding either or both of the light and heavy chains that is not necessary for binding to BAI1. The molecules expressed from such truncated DNA molecules are also encompassed by the antibodies, or antigen-binding fragments thereof, described herein.

In addition, bifunctional antibodies, or antigen-binding fragments thereof, can be produced in which one heavy and one light chain are an antibody of the disclosure and the other heavy and light chain are specific for an antigen other than BAI1 by crosslinking an antibody of the disclosure to a second antibody by standard chemical crosslinking methods. Bifunctional antibodies can also be made by expressing a nucleic acid engineered to encode a bifunctional antibody.

For recombinant expression of the antibodies, or antigen-binding fragments thereof, described herein, the host cell can be co-transfected with two expression vectors of the disclosure, the first vector encoding a heavy chain derived polypeptide and the second vector encoding a light chain derived polypeptide. Typically, the two vectors each contain a separate selectable marker. Alternately, a single vector can be used which encodes both heavy and light chain polypeptides.

Once a nucleic acid encoding one or more portions of the antibodies, or antigen-binding fragments thereof, with desired CDR sequences is generated, further alterations can be introduced into the coding sequence, for example, to generate nucleic acids encoding antibodies with different CDR sequences, antibodies with reduced affinity to the Fc receptor, or antibodies of different subclasses.

The antibodies, or antigen-binding fragments thereof, described herein can also be produced by chemical synthesis (such as by the methods described in Solid Phase Peptide Synthesis, 2nd ed., 1984 The Pierce Chemical Co., Rockford, Ill.). Variant antibodies, or antigen-binding fragments thereof, can also be generated using a cell-free platform (see, Chu et al., Biochemia, 2001, 2).

Once antibodies, or antigen-binding fragments thereof, described herein have been produced by recombinant expression, they can be purified by any method known in the art for purification of an immunoglobulin molecule, for example, by chromatography (such as ion exchange, affinity, particularly by affinity for Protein A, Protein G or Protein L selection, and sizing column chromatography), centrifugation, differential solubility, or by any other standard technique for the purification of proteins. Further, the antibodies, or antigen-binding fragments thereof, described herein can be fused to heterologous polypeptide sequences described herein or otherwise known in the art to facilitate purification.

Once isolated, the antibodies, or antigen-binding fragments thereof, can, if desired, be further purified, such as by high performance liquid chromatography (see, Fisher, Laboratory Techniques In Biochemistry And Molecular Biology (Work and Burdon, eds., Elsevier, 1980)), or by gel filtration chromatography on a Superdex™ 75 column (Pharmacia Biotech AB, Uppsala, Sweden).

The present disclosure provides vectors comprising any of the nucleic acid molecules described herein. The present disclosure also provides prokaryotic host cells transformed with the vector. The present disclosure also provides eukaryotic host cells transformed with the vector. In some embodiments, the eukaryotic host cell is a mammalian host cell.

In some embodiments, the antibodies, or antigen-binding fragments thereof, are conjugated to an effector moiety. In some embodiments, the antibodies, or antigen-binding fragments thereof, are modified by the covalent attachment of any type of molecule to the antibodies, or antigen-binding fragments thereof, such that covalent attachment does not interfere with binding to BAI1. In some embodiments, the effector moiety is a detectable label, a cytotoxic agent, a chemotherapeutic agent, or a nucleic acid molecule. The effector moiety can also be an antineoplastic agent, a drugs, a toxin, a biologically active protein (such as an enzyme), another antibody or antibody fragment, a synthetic or naturally occurring polymer, a nucleic acid molecule, a radionuclides (such as radioiodide), a radioisotope, a chelated metal, a nanoparticle, or a reporter group (such as a fluorescent compound or a compound which can be detected by NMR or ESR spectroscopy).

In some embodiments, the antibodies, or antigen-binding fragments thereof, can be conjugated to a cytotoxic agent, a radionuclide, or a drug moiety to modify a particular biological response. The effector moiety can be a protein or polypeptide, such as, for example, a toxin (such as abrin, ricin A, saporin, Pseudomonas exotoxin, diphtheria toxin, ethidium bromide or PE40, PE38, gelonin, RNAse, peptide nucleic acids (PNAs), ribosome inactivating protein (RIP) type-1 or type-2, pokeweed anti-viral protein (PAP), bryodin, momordin, chemotherapeutic agents, and bouganin), a signaling molecule (such as α-interferon, β-interferon, nerve growth factor, platelet derived growth factor or tissue plasminogen activator), a thrombotic agent or an anti-angiogenic agent (such as, angiostatin or endostatin) or a biological response modifier such as a cytokine or growth factor (such as, interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In some embodiments, the cytotoxic agent is a small molecule, a prodrug, a maytansinoid, or a toxin. In some embodiments, the antibody, or antigen-binding fragment thereof, comprises from 3 to 5 maytansinoid molecules per antibody, or antigen-binding fragment thereof. In some embodiments, the maytansinoid is conjugated to the antibody, or antigen-binding fragment thereof, by a chemical linker chosen from N-succinimidyl-3-(2-pyridyldithio) propionate, N-succinimidyl-4-(2-pyridylthio)pentanoate (SPP), and succinimidyl-4-(N-maleimidomethyl)cyclohexanal-1-carboxylate. In some embodiments, the cytotoxic agent is taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, or puromycin.

In some embodiments, the detectable label is radioactive compound, a fluorescent compound, a chromophore, an enzyme, an imaging agent, a metal ion, or a substrate. In some embodiments, a fluorescent moiety includes, but is not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase, and the like.

In some embodiments, the effector moiety is an antimetabolite (such as, methotrexate, 6-mercaptopurine, 6-thioguanine, cytarabine, and 5-fluorouracil decarbazine), an alkylating agent (such as, mechlorethamine, thioepa chlorambucil, melphalan, carmustine (BSNU) and lomustine (CCNU), cyclothosphamide, busulfan, dibromomannitol, streptozotocin, mitomycin C5 and cisdichlorodiamine platinum (II) (DDP) cisplatin), an anthracycline (such as, daunorubicin (formerly daunomycin) and doxorubicin), an antibiotic (such as, dactinomycin (formerly actinomycin), bleomycin, mithramycin, anthramycin (AMC), calicheamicins or duocarmycins), or an anti-mitotic agent (such as, vincristine and vinblastine).

In some embodiments, the radionuclides is, but is not limited to, $^{13}$N, $^{18}$F, $^{32}$F, $^{64}$Cu, $^{66}$Ga, $^{67}$Ga, $^{68}$Ga, $^{67}$Cu, $^{77}$Br, $^{80m}$Br, $^{82}$Rb, $^{86}$Y, $^{90}$Y, $^{95}$Ru, $^{97}$Ru, $^{99m}$Tc, $^{103}$Ru, $^{105}$Ru, $^{111}$In, $^{113m}$In, $^{113}$Sn, $^{121m}$Te, $^{122m}$Te, $^{125m}$Te, $^{123}$I, $^{124}$I, $^{125}$I, $^{126}$I, $^{131}$I, $^{133}$I, $^{165}$Tm, $^{167}$Tm, $^{168}$Tm, $^{177}$Lu, $^{186}$Re, $^{188}$Re, $^{195m}$Hg, $^{211}$At, $^{212}$Bi, $^{213}$Bi, and $^{225}$Ac.

In some embodiments, the chemotherapeutic agent is cisplatin, carboplatin, oxaliplatin, nedaplatin, triplatin tetranitrate, phenanthriplatin, picoplatin, satraplatin, methotrexate, vincristine, doxorubicin, tunicamycin, oligomycin, bortezomib, MG132, 5-flurouracil, sorafenib, flavopiridol, gemcitabine, taxol, mercaptopurine, thioguanine, hydroxyurea, cytarabine, mitomycin, cyclophosphamide, ifosfamide, nitrosourea, dacarbazine, procarbazine, an etoposide, a campathecin, bleomycin, idarubicin, daunorubicin, dactinomycin, distamycin A, ethidium, netropsin, auristatin, amsacrine, prodigiosin, bortezomib, pibenzimol, togamycin, duocarmycin SA, plicamycin, mitoxantrone, asparaginase, vinblastine, vinorelbine, paclitaxel, docetaxel, CPT-11, gleevec, erlotinib, gefitinib, ibrutinib, crizotinib, ceritinib, lapatinib, navitoclax, or regorafenib.

In some embodiments, the nucleic acid molecule is a single layer nucleic acid carrier, a 1.5 layer nucleic acid carrier, a two layer nucleic acid carrier, a 2.5 layer nucleic acid carrier, or a three layer nucleic acid carrier (such as those disclosed in, for example, PCT Publications WO 17/143156 and WO 17/143171).

Techniques for conjugating such effector moieties to antibodies are well known in the art (see, Hellstrom et al., Controlled Drug Delivery, 2nd Ed., at pages 623-53 (Robinson et al., eds., 1987)); Thorpe et al., Immunol. Rev., 1982, 62, 119-58; and Dubowchik et al., Pharmacology and Therapeutics, 1999, 83, 67-123).

In some embodiments, the antibodies, or antigen-binding fragments thereof, can be fused via a covalent bond (such as, a peptide bond), through the antibody's N-terminus or C-terminus or internally, to an amino acid sequence of another protein (or portion thereof; for example, at least a 10, 20 or 50 amino acid portion of the protein). The antibodies, or antigen-binding fragments thereof, can linked to the other protein at the N-terminus of the constant domain of the antibody. Recombinant DNA procedures can be used to create such fusions, for example, as described in PCT Publication WO 86/01533 and European Patent EP0392745. In some embodiments, the effector moiety can increase half-life in vivo, and/or enhance the delivery of an antibody across an epithelial barrier to the immune system. Examples of suitable effector moieties of this type include polymers, albumin, albumin-binding proteins or albumin-binding compounds such as those described in PCT Publication WO 2005/117984.

In some embodiments, the antibodies, or antigen-binding fragments thereof, can be conjugated to a small molecule toxin. In some embodiments, the antibodies, or antigen-binding fragments thereof, can be conjugated to a dolastatin or a dolastatin peptidic analog or derivative, such as an auristatin (see, U.S. Pat. Nos. 5,635,483 and 5,780,588). The dolastatin or auristatin drug moiety may be attached to the antibody through its N-terminus, C-terminus or internally (see, PCT Publication WO 02/088172). Exemplary auristatin embodiments include the N-terminus linked monomethylauristatin drug moieties DE and DF, as disclosed in U.S. Pat. No. 7,498,298 (disclosing linkers and methods of preparing monomethylvaline compounds such as MMAE and MMAF conjugated to linkers).

Antibodies, or antigen-binding fragments thereof, can also be conjugated to liposomes for targeted delivery (see, Park et al., Adv. Pharmacol., 1997, 40, 399-435; and Marty et al., Methods Molec. Med., 2004, 109, 389-401).

In some embodiments, the antibodies, or antigen-binding fragments thereof, can be attached to poly(ethyleneglycol) (PEG) moieties. In some embodiments, the antibodies, or antigen-binding fragments thereof, and the PEG moieties can be attached through any available amino acid side-chain or terminal amino acid functional group located in the antibodies, or antigen-binding fragments thereof, for example, any free amino, imino, thiol, hydroxyl or carboxyl group. Such amino acids can occur naturally in the antibodies, or antigen-binding fragments thereof, or can be engineered into the fragment using recombinant DNA methods (see, U.S. Pat. No. 5,219,996). Multiple sites can be used to attach two or more PEG moieties. PEG moieties can be covalently linked through a thiol group of at least one cysteine residue located in the antibodies, or antigen-binding fragments thereof. Where a thiol group is used as the point of attachment, appropriately activated effector moieties, for example, thiol selective derivatives such as maleimides and cysteine derivatives, can be used.

In some embodiments, the antibodies, or antigen-binding fragments thereof, can comprise a modified Fab' fragment which is PEGylated. The PEG moiety can be attached to a cysteine in the hinge region. In some embodiments, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

In some embodiments, the antigen-binding fragment can be an Fab, an F(ab')$_2$, an Fv, an scFv, an scFv-Fc, a diabody, or a minibody fragment. In some embodiments, the antigen-binding fragment can be an Fab fragment. In some embodiments, the antigen-binding fragment can be an F(ab')$_2$ fragment. In some embodiments, the antigen-binding fragment can be an Fv fragment. In some embodiments, the antigen-binding fragment can be an scFv fragment. In some embodiments, the antigen-binding fragment can be an scFv-Fc fragment. In some embodiments, the antigen-binding fragment can be a diabody fragment. In some embodiments, the antigen-binding fragment can be a minibody fragment.

The present disclosure also provides pharmaceutical compositions comprising the antibodies, or antigen-binding fragments thereof, described herein and a pharmaceutically acceptable carrier. In some embodiments, the pharmaceutical compositions further comprise a tonicity agent, a surfactant, a preservative, and/or a buffer system having a pH of about 4.0 to about 8.0. In some embodiments, the pharmaceutical compositions further comprise one or more additional therapeutic agents, such as the combination therapeutic agents described herein. In some embodiments, the pharmaceutical composition is a liquid pharmaceutical composition.

In some embodiments, the pharmaceutical compositions can be presented in unit dose forms containing a predetermined amount of an antibody, or antigen-binding fragment thereof, described herein per dose. Pharmaceutically acceptable carriers for use in the pharmaceutical compositions can take a wide variety of forms depending on the condition to be treated or route of administration.

Pharmaceutical compositions comprising the antibodies, or antigen-binding fragments thereof, described herein can be prepared for storage as lyophilized formulations or aqueous solutions by mixing the antibodies, or antigen-binding fragments thereof, having the desired degree of purity with optional pharmaceutically acceptable carriers, excipients or stabilizers typically employed in the art (all of which are referred to herein as "carriers") such as, for example, buffering agents, stabilizing agents, preservatives, isotonifiers, non-ionic detergents, antioxidants, and other miscellaneous additives.

Buffering agents help to maintain the pH in the range that approximates physiological conditions. They can be present at concentration ranging from about 2 mM to about 50 mM. Suitable buffering agents for use in the pharmaceutical compositions described herein can include both organic and inorganic acids and salts thereof, such as citrate buffers (such as, monosodium citrate-disodium citrate mixture, citric acid-trisodium citrate mixture, citric acid-monosodium citrate mixture, and the like), succinate buffers (such as, succinic acid monosodium succinate mixture, succinic acid-sodium hydroxide mixture, succinic acid-disodium succinate mixture, and the like), tartrate buffers (such as, tartaric acid-sodium tartrate mixture, tartaric acid-potassium tartrate mixture, tartaric acid-sodium hydroxide mixture, and the like), fumarate buffers (such as, fumaric acid-monosodium fumarate mixture, fumaric acid-disodium fumarate mixture, monosodium fumarate-disodium fumarate mixture, and the like), gluconate buffers (such as, gluconic acid-sodium gluconate mixture, gluconic acid-sodium hydroxide mixture, gluconic acid-potassium glyconate mixture, and the like), oxalate buffer (such as, oxalic acid-sodium oxalate mixture, oxalic acid-sodium hydroxide mixture, oxalic acid-potassium oxalate mixture, and the like), lactate buffers (such as, lactic acid-sodium lactate mixture, lactic acid-sodium hydroxide mixture, lactic acid-potassium lactate mixture, and the like) and acetate buffers (such as, acetic acid-sodium acetate mixture, acetic acid-sodium hydroxide mixture, and the like). Additionally, phosphate buffers, histidine buffers and trimethylamine salts, such as Tris, can be used.

Preservatives can be added to the pharmaceutical compositions to decrease microbial growth, and can be added in amounts ranging from about 0.2% to about 1% (w/v). Suitable preservatives for use with the pharmaceutical compositions described herein include, but are not limited to, phenol, benzyl alcohol, meta-cresol, methyl paraben, propyl paraben, octadecyldimethylbenzyl ammonium chloride, benzalkonium halides (such as, chloride, bromide, and iodide), hexamethonium chloride, and alkyl parabens such as methyl or propyl paraben, catechol, resorcinol, cyclohexanol, and 3-pentanol.

Isotonicifiers sometimes known as "stabilizers" can be added to ensure isotonicity of liquid compositions and include polyhydric sugar alcohols, for example, trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (such as, peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in the range from about 0.1 to about 10,000 weights per part of weight active protein.

Non-ionic surfactants or detergents (also known as "wetting agents") can also be added to pharmaceutical compositions help solubilize the antibodies, or antigen-binding fragments thereof, as well as to protect the antibodies, or antigen-binding fragments thereof, described herein against agitation-induced aggregation, which also permits the formulation to be exposed to shear surface stressed without causing denaturation of the proteins. Suitable non-ionic surfactants include polysorbates (20, 80, etc.), polyoxamers (184, 188 etc.), Pluronic polyols, polyoxyethylene sorbitan monoethers (TWEEN™-20, TWEEN™-80, and the like). Nonionic surfactants can be present in a range of about 0.05 mg/mL to about 1.0 mg/mL, for example, about 0.07 mg/mL to about 0.2 mg/mL.

Additional excipients, such as, bulking agents (such as, starch), chelating agents (such as, EDTA), antioxidants (such as, ascorbic acid, methionine, and vitamin E), and cosolvents can also be added to the pharmaceutical compositions.

The present disclosure also provides pharmaceutical kits containing the antibodies, or antigen-binding fragments thereof, including antibody conjugates, described herein. The pharmaceutical kits can be a package comprising the antibodies, or antigen-binding fragments thereof, described herein (such as, either in lyophilized form or as an aqueous solution) and one or more of the following: a combination therapeutic agent, a device for administering the antibodies, or antigen-binding fragments thereof, such as a pen, needle and/or syringe; and pharmaceutical grade water or buffer to re-suspend the antibodies, or antigen-binding fragments thereof, if the antibody is in lyophilized form.

In some embodiments, each unit dose of the antibodies, or antigen-binding fragments thereof, is packaged separately, and a kit can contain one or more unit doses (such as, two unit doses, three unit doses, four unit doses, five unit doses, eight unit doses, ten unit doses, or more). In some embodiments, the one or more unit doses are each housed in a syringe or pen.

Diagnostic kits containing the antibodies, or antigen-binding fragments thereof, (including antibody conjugates), described herein are also encompassed herein. The diagnostic kit can be a package comprising the antibodies, or antigen-binding fragments thereof, described herein (such as, either in lyophilized form or as an aqueous solution) and one or more reagents useful for performing a diagnostic assay. Where the antibodies, or antigen-binding fragments thereof, are labeled with an enzyme, the kits can include substrates and cofactors required by the enzyme (such as, a substrate precursor which provides the detectable chromophore or fluorophore). In addition, other additives can be included, such as stabilizers, buffers (such as, a block buffer or lysis buffer), and the like. In some embodiments, the antibodies, or antigen-binding fragments thereof, included in a diagnostic kit can be immobilized on a solid surface, or a solid surface (such as, a slide or plate) on which the antibodies, or antigen-binding fragments thereof, can be immobilized is included in the kit. The relative amounts of the various reagents can be varied to provide for concentrations in solution of the reagents which substantially optimize the sensitivity of the assay. In some embodiments, the antibodies, or antigen-binding fragments thereof, and one or more reagents can be provided (individually or combined) as dry powders, usually lyophilized, including excipients which on dissolution will provide a reagent solution having the appropriate concentration.

The present disclosure also provides methods of detecting a cell expressing BAI1, the methods comprising contacting the cell with the antibodies, or antigen-binding fragments thereof, described herein, and detecting the antibodies, or antigen-binding fragments thereof. In some embodiments, the cell is present in a biological sample obtained from a human and the cell is contacted with the antibody, or antigen-binding fragment thereof, in vitro. In some embodiments, the cell is present in a human and the cell is contacted with the antibody, or antigen-binding fragment thereof, in vivo.

In some embodiments, the antibodies, or antigen-binding fragments thereof, described herein have a high binding affinity for BAI1. In some embodiments, the antibodies, or antigen-binding fragments thereof, have particular association rate constants ($k_{on}$ or $k_A$ values), dissociation rate constants ($k_{off}$ or $k_D$ values), affinity constants ($K_A$ values), dissociation constants ($K_D$ values) and/or $IC_{50}$ values.

In some embodiments, the antibodies, or antigen-binding fragments thereof, bind to BAI1 with a $K_A$ ($k_{on}/k_{off}$) of at least about $10^{10}$ $M^{-1}$, at least about $4 \times 10^{11}$ $M^{-1}$, at least about $10^{11}$ $M^{-1}$, at least about $4 \times 10^{12}$ $M^{-1}$, at least about $10^{12}$ $M^{-1}$, at least about $4 \times 10^{13}$ $M^{-1}$, at least about $10^{13}$ $M^{-1}$, at least about $4 \times 10^{14}$ $M^{-1}$, at least about $10^{14}$ $M^{-1}$, at least about $4 \times 10^{15}$ $M^{-1}$, or at least about $10^{15}$ $M^{-1}$, or with a $K_A$ of any range from and to any pair of the foregoing values (such as, from about $4 \times 10^{11}$ $M^{-1}$ to about $4 \times 10^{13}$ $M^{-1}$ or from about $4 \times 10^{12}$ $M^{-1}$ to about $4 \times 10^{15}$ $M^{-1}$).

In some embodiments, the antibodies, or antigen-binding fragments thereof, bind to BAI1 with a $K_D$ ($k_{off}/k_{on}$) of about $10^{-10}$ or less, about $4 \times 10^{-11}$ M or less, about $10^{-11}$ M or less, about $4 \times 10^{-12}$ M or less, about $10^{-12}$ M or less, about $4 \times 10^{13}$ M or less, about $10^{-13}$ M or less, about $4 \times 10^{14}$ M or less, about $10^{-14}$ M or less, about $4 \times 10^{-15}$ M or less, or about $10^{-15}$ M or less, or with a $K_D$ of any range from and to any pair of the foregoing values (such as, from about $4\times10^{-11}$ M to about $4\times10^{-13}$ M or from about $4\times10^{-12}$ M to about $4\times10^{-15}$ M).

In some embodiments, the $K_D$ ($k_{off}/k_{on}$) value is determined by assays well known in the art, such as ELISA, isothermal titration calorimetry (ITC), fluorescent polarization assay or any other biosensors such as BIAcore.

In some embodiments, the antibodies, or antigen-binding fragments thereof, bind to BAI1 and inhibit the binding of BAI1 to its ligand at an $IC_{50}$ of less than about 0.02 nM, less than about 0.01 nM, less than about 0.005 nM, less than about 0.002 nM, less than about 0.001 nM, less than about $5\times10^{-4}$ nM, less than about $2\times10^{-4}$ nM, less than about $1\times10^{-4}$ nM, less than about $5\times10^{-5}$ nM, less than about $2\times10^{-4}$ nM, less than about $1\times10^{-4}$ nM, less than about $5\times10^{-6}$ nM, less than about $2\times10^{-6}$ nM, less than about $1\times10^{-6}$ nM, less than about $5\times10^{-7}$ nM, less than about $2\times10^{-7}$ nM, or less than about $1\times10^{-7}$ nM, or with an $IC_{50}$ of any range from and to any pair of the foregoing values (such as, from about 0.02 nM to about $2\times10^{-5}$ nM, or from about $5\times10^{-5}$ nM to about $1\times10^{-7}$ nM). The $IC_{50}$ can be measured according to methods well known in the art, such as ELISA.

The antibodies, or antigen-binding fragments thereof, including those antibodies that have been modified, such as by biotinylation, horseradish peroxidase, or any other detectable moiety (including those described above), can be used for diagnostic purposes.

In some embodiments, the antibodies, or antigen-binding fragments thereof, can be used to purify or detect BAI1, including both in vitro and in vivo diagnostic methods. For example, the antibodies, or antigen-binding fragments thereof, can be used in immunoassays for qualitatively and quantitatively measuring levels of BAI1 in biological samples, or to identify the location, quantity, behavior and/or the like of BAI1 in an animal. For example, measuring levels of BAI1 using the antibodies, or antigen-binding fragments thereof, described herein can be used to, for example: 1) diagnose or determine an increased risk of developing a cancer in a patient, 2) determine the prognosis of a patient, including the stage and grade of a tumor (particularly whether the cancer is metastatic or likely to be metastatic) and/or its potential sensitivity to BAI1 therapy, 3) determine the origin of a tumor, and/or 4) determine the efficacy of a treatment of a patient.

In some embodiments, the antibodies, or antigen-binding fragments thereof, can be used, for example, in conjunction with compound screening assays, for the evaluation of the effect of pharmaceutical agents on the expression and/or activity of the BAI1 gene product. Additionally, the antibodies, or antigen-binding fragments thereof, can be used in conjunction with gene therapy techniques to, for example, evaluate the success of transfection of normal and/or engineered BAI1-expression.

The present disclosure also provides methods of diagnosis of a neurological disease comprising detecting the amount or activity of BAI1 expressed in neural tissue or in any tissue associated with a non-CNS target organ, such as the lung, liver, kidney, spleen, and the like. The diagnostic methods can employ the antibodies, or antigen-binding fragments thereof, conjugated to a diagnostic agent. The antibodies, or antigen-binding fragments thereof, can be used diagnostically, for example, to detect expression of BAI1 in particular cells, tissues, or serum; or to monitor the development or progression of an immunologic response as part of a clinical testing procedure to, for example, determine the efficacy of a particular treatment regimen. Detection can be facilitated by coupling the antibodies, or antigen-binding fragments thereof, to a detectable substance. Examples of detectable substances include, but are not limited to, various enzymes, prosthetic groups, fluorescent materials (such as, fluorescein and rhodamine and their derivatives), luminescent materials, bioluminescent materials, optical agents (such as, derivatives of phorphyrins, anthraquinones, anthrapyrazoles, perylenequinones, xanthenes, cyanines, acridines, phenoxazines and phenothiazines), radioactive materials, positron emitting metals using various positron emission tomographies, and nonradioactive paramagnetic metal ions (such as, Gd(III), Eu(III), Dy(III), Pr(III), Pa(IV), Mn(II), Cr(III), Co(III), Fe(III), Cu(II), Ni(II), Ti(III), and V(IV)). The detectable substance can be coupled or conjugated either directly to the antibodies, or antigen-binding fragments thereof, or indirectly, through an intermediate (such as, for example, a linker known in the art) using techniques known in the art. Examples of enzymatic labels include luciferases (such as, firefly luciferase and bacterial luciferase; see, U.S. Pat. No. 4,737,456), luciferin, 2,3-dihydrophthalazinediones, malate dehydrogenase, urease, peroxidase such as horseradish peroxidase (HRPO), alkaline phosphatase, (3-galactosidase, acetylcholinesterase, glucoamylase, lysozyme, saccharide oxidases (such as, glucose oxidase, galactose oxidase, and glucose-6-phosphate dehydrogenase), heterocyclic oxidases (such as, uricase and xanthine oxidase), lactoperoxidase, microperoxidase, and the like. Examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include, but are not limited to, luciferase, luciferin, and aequorin; and examples of suitable radioactive material include, but are not limited to, $^{125}$I, $^{131}$I, $^{111}$In, or $^{99}$Tc.

The disclosure also provides methods for detecting expression of BAI1 on a cell, comprising contacting a biological sample from a patient using one or more of the antibodies, or antigen-binding fragments thereof, described herein (optionally conjugated to detectable moiety), and detecting whether or not the sample is positive for BAI1 expression, or whether the sample has altered (such as, reduced or increased) expression as compared to a control sample. The biological sample may include biopsies of various tissues including, without limitation: skin, muscle, breast, prostate, cervical, ovarian, brain, testicular, and pulmonary. Cellular examples of biological samples include tumor cells, skin cells, muscle cells, blood cells, ovarian cells, brain cells, prostate cells, breast cells, testicular cells, cervical cells, and lung cells. The biological sample may also be a biological fluid.

The presence of BAI1-expressing cells in a biological sample is indicative of the presence of cancer and may be indicative of metastases, particularly when present in quantities greater than that of normal healthy subjects. The loss of BAI1-expressing cells in a patient, particularly one undergoing treatment, over time is indicative of remission (i.e., successful treatment), while the lack of change in BAI1-expressing cell levels in a patient undergoing treatment is indicative of resistance to the therapy and indicates that a different therapeutic strategy could be employed. Similarly, the gain of BAI1-expressing cells in a patient over time can be indicative of recurrence. Additionally, the imaging techniques described herein may be employed to monitor the size of the tumor to determine the efficacy of a treatment. In some embodiments, other cancer diagnostic assays can be performed to confirm the results obtained with the methods described herein.

In some embodiments, a biological sample (such as, a tumor sample) can be obtained from a subject and the presence of BAI1-expressing cells determined. The number of BAI1-expressing cells can be correlated with tumor grade. In some embodiments, the number of BAI1-expressing cells in the biological sample is compared to the number of BAI1-expressing cells in a corresponding biological sample from a healthy individual to determine the modulation of BAI1-expressing cells in the tumor. Subjects comprising the tumor can be treated with pharmaceutical agents to modulate the activity of BAI1-expressing cells to normal, healthy levels.

Diseases that can be diagnosed using the present methods include, but are not limited to, neurological cancers such as primary brain tumors including glioma (glioblastoma), meningioma, neurinoma, pituitary adenoma, medulloblastoma, craniopharyngioma, hemangioma, epidermoid, sarcoma and intracranial metastasis from other tumor sources. In some embodiments, the antibodies, or antigen-binding fragments thereof, described herein can be used to diagnose glioblastoma multiforme (GBM).

The present disclosure also provides methods of treating a cancer expressing BAI1, the methods comprising administering to a human patient in need thereof the antibodies, or antigen-binding fragments thereof, described herein. In some embodiments, the methods involve administering to a human patient having a solid tumor an amount of the antibodies, or antigen-binding fragments thereof, described herein to provide therapeutic benefit.

In some embodiments, the antibodies, or antigen-binding fragments thereof, described herein can be administered to a patient by a variety of routes such as orally, transdermally, subcutaneously, intranasally, intravenously, intraarterially, intramuscularly, intraocularly, topically, locally, intrathecally, intracerebroventricularly, intraspinally, and intracranially. The most suitable route for administration in any given case will depend on the particular antibody, the subject, and the nature and severity of the disease and the physical condition of the subject. In some embodiments, the antibodies, or antigen-binding fragments thereof, can be formulated as an aqueous solution. In some embodiments, the antibodies, or antigen-binding fragments thereof, are administered intravenously or intracranially.

The antibodies, or antigen-binding fragments thereof, described herein can be used to treat various BAI1-expressing neoplasms. In some embodiments, the antibodies, or antigen-binding fragments thereof, described herein can be used to treat BAI1-expressing cancers, such as sarcomas with properties of skeletal muscle, and skin tumors. In some embodiments, the antibodies, or antigen-binding fragments thereof, described herein can be used to treat BAI1-expressing neurological cancers, such as a brain tumor or a small brain lesion, such as micrometastases, in a patient. In some embodiments, the BAI1 expressing cancer is a neurological cancer. In some embodiments, the neurological cancer is a primary brain tumor, a glioblastoma, a glioma, a meningioma, a neurinoma, a pituitary adenoma, a medulloblastoma, a craniopharyngioma, a hemangioma, an epidermoid, a sarcoma, or an intracranial metastasis from other tumor sources. In some embodiments, the neurological cancer is a glioblastoma. In some embodiments, the glioblastoma is glioblastoma multiforme (GBM).

In some embodiments, the BAI1-expressing brain tumor is a GBM tumor containing GBM tumor-initiating cells. In some embodiments, treatment with the antibodies, or antigen-binding fragments thereof, described herein results in the inhibition of the proliferation of GBM tumor-initiating cells. In some embodiments, the antibodies, or antigen-binding fragments thereof, further inhibit self-renewal of GBM tumor-initiating cells. Inhibition of cell proliferation and/or self-renewal may lead to improvement in the signs or symptoms of disease. For example, such therapy may result in an improvement in survival (overall survival and/or progression free survival) and/or may result in an objective clinical response (partial or complete). In some embodiments, the antibodies, or antigen-binding fragments thereof, are internalized by the GBM tumor cell, resulting in increased therapeutic efficacy of the antibodies, or antigen-binding fragments thereof, in killing the GBM tumor cell to which it binds. In some embodiments, the antibodies, or antigen-binding fragments thereof, act as antagonists of BAH biological activity, and can additionally be used as a method for the inhibition of abnormal BAI1 activity.

In some embodiments, the antibodies, or antigen-binding fragments thereof, are useful in the treatment of non-neurological BAI1-expressing tumors, including cancers and benign tumors. Cancers that are amenable to treatment by the antibodies, or antigen-binding fragments thereof, described herein include those that overexpress BAI1. In some embodiments, cancers that are amenable to treatment by the antibodies, or antigen-binding fragments thereof, described herein include epithelial cell cancers. In some embodiments, cancers that are amenable to treatment by the antibodies, or antigen-binding fragments thereof, described herein include, but are not limited to, breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, cancer of the thymus, head and neck cancer, and colorectal cancer. The cancer may be newly diagnosed and naive to treatment, or may be relapsed, refractory, or relapsed and refractory, or a metastatic form of a solid tumor.

In some embodiments, the antibodies, or antigen-binding fragments thereof, described herein can be used in the treatment of a BAI1-expressing blood malignancy, including, but not limited to, myelomas (such as, multiple myeloma), lymphomas (such as, Hodgkin's lymphoma, non-Hodgkin's lymphoma, Waldenström's macroglobulinemia, and mantle cell lymphoma), leukemias (such as, chronic lymphocytic leukemia, acute myeloid leukemia, and acute lymphocytic leukemia), and myelodysplastic syndromes. In some embodiments, the methods comprise administering to a human patient having a blood malignancy the antibodies, or antigen-binding fragments thereof, described herein to provide therapeutic benefit.

In some embodiments, the administration of the antibodies, or antigen-binding fragments thereof, described herein is repeated after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens, a patient can receive anti-BAI1 therapy for a prolonged period of time, such as 6 months, 1 year, or more. The amount of the antibodies, or antigen-binding fragments thereof, described herein administered to the patient is a therapeutically effective amount. As used herein, a "therapeutically effective" amount of the antibodies, or antigen-binding fragments thereof, described herein can be administered as a single dose or over the course of a therapeutic regimen, such as over the course of a week, two weeks, three weeks, one month, three months, six months, one year, or longer. Exemplary therapeutic regimens are further described herein. Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

The use of the antibodies, or antigen-binding fragments thereof, described herein to treat cancer in a patient can result in any demonstrated clinical benefit compared with no therapy (when appropriate) or to a known standard of care. Clinical benefit can be assessed by any method known to one of ordinary skill in the art. In some embodiments, clinical benefit is assessed based on objective response rate (ORR) (determined using RECIST version 1.1), duration of response (DOR), progression-free survival (PFS), and/or overall survival (OS). In some embodiments, a complete response indicates therapeutic benefit. In some embodiments, a partial response indicates therapeutic benefit. In some embodiments, stable disease indicates therapeutic benefit. In some embodiments, an increase in overall survival indicates therapeutic benefit. In some embodiments, therapeutic benefit may constitute an improvement in time to disease progression and/or an improvement in symptoms or quality of life. In some embodiments, a therapeutic benefit may not translate to an increased period of disease control, but rather a markedly reduced symptom burden resulting in improved quality of life. As will be apparent to those of skill in the art, a therapeutic benefit may be observed using the antibodies, or antigen-binding fragments thereof, described herein alone (monotherapy) or adjunctive to, or with, other anti-cancer therapies and/or targeted or non-targeted anti-cancer agents.

In some embodiments, a therapeutic benefit can be assessed using standard clinical tests designed to measure the response to a new treatment for cancer. To assess the therapeutic benefits of the antibodies, or antigen-binding fragments thereof, described herein one or a combination of the following tests can be used: 1) the Response Evaluation Criteria In Solid Tumors (RECIST) version 1.1; 2) immune-related RECIST (irRECIST); 3) the Eastern Cooperative Oncology Group (ECOG) Performance Status; 4) immune-related response criteria (irRC); 5) disease evaluable by assessment of tumor antigens; 6) validated patient reported outcome scales; and/or 7) Kaplan-Meier estimates for overall survival and progression free survival.

The present disclosure also provides combination therapy methods comprising administering at least two agents to a patient, the first of which is an antibody, or antigen-binding fragment thereof, described herein, and the second of which is a combination therapeutic agent. The antibodies, or antigen-binding fragments thereof, described herein and the combination therapeutic agent can be administered simultaneously, sequentially, or separately. The combinatorial therapy methods can result in a greater than additive effect.

In the present methods, the antibodies, or antigen-binding fragments thereof, described herein and the combination therapeutic agent can be administered concurrently, either simultaneously or successively. The antibodies, or antigen-binding fragments thereof, described herein and the combination therapeutic agent are administered successively if they are administered to the patient on the same day, for example, during the same patient visit. Successive administration can occur 1, 2, 3, 4, 5, 6, 7 or 8 hours apart. In contrast, the antibodies, or antigen-binding fragments thereof, described herein and the combination therapeutic agent are administered separately if they are administered to the patient on different days, for example, the antibodies, or antigen-binding fragments thereof, and the combination therapeutic agent can be administered at a 1-day, 2-day or 3-day, one-week, 2-week or monthly intervals. In the methods of the present disclosure, administration of the antibodies, or antigen-binding fragments thereof, described herein can precede or follow administration of the combination therapeutic agent. In some embodiments, the antibodies, or antigen-binding fragments thereof, described herein and combination therapeutic agent can be administered concurrently for a period of time, followed by a second period of time in which the administration of the antibodies, or antigen-binding fragments thereof, and the combination therapeutic agent is alternated.

In some embodiments, the combination therapeutic agent is a chemotherapeutic agent, an anti-angiogenic agent, an anti-rheumatic drug, an anti-inflammatory agent, a radiotherapeutic, an immunosuppressive agent, or a cytotoxic drug. The antibodies, or antigen-binding fragments thereof, described herein can be used in combination with conventional cancer therapies, such as surgery, radiotherapy, chemotherapy, or combinations thereof. In some embodiments, the methods further comprise one or both of surgically resecting tumor cells and/or administering radiation therapy. In some embodiments, other therapeutic agents useful for combination tumor therapy with the antibodies, or antigen-binding fragments thereof, described herein include antagonists, such as, antibodies, of other factors that are involved in tumor growth, such as HER2, HER3, HER4, VEGF, or TNF-α. In some embodiments, for treatment of cancers it may be beneficial to also administer one or more cytokines to the patient. In some embodiments, the antibodies, or antigen-binding fragments thereof, described herein is co-administered with a growth inhibitory agent.

For treatment of cancers, anti-inflammatory agents can suitably be used in combination with the antibodies, or antigen-binding fragments thereof, described herein. Anti-inflammatory agents include, but are not limited to, acetaminophen, diphenhydramine, meperidine, dexamethasone, pentasa, mesalazine, asacol, codeine phosphate, benorylate, fenbufen, naprosyn, diclofenac, etodolac and indomethacin, aspirin, and ibuprofen.

For treatment of cancers, chemotherapeutic agents can be used in combination with the antibodies, or antigen-binding fragments thereof, described herein. Chemotherapeutic agents include, but are not limited to, radioactive molecules, toxins (such as cytotoxins or cytotoxic agents) which include any agent that is detrimental to the viability of cells, agents, and liposomes or other vesicles containing chemotherapeutic compounds. Examples of suitable chemotherapeutic agents include, but are not limited to, 1-dehydrotestosterone, 5-fluorouracil decarbazine, 6-mercaptopurine, 6-thioguanine, actinomycin D, adriamycin, aldesleukin, an anti-α5β1 integrin antibody, alkylating agents, allopurinol sodium, altretamine, amifostine, anastrozole, anthramycin (AMC)), anti-mitotic agents, cisdichlorodiamine platinum (II) (DDP) cisplatin, diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), chlorambucil, cisplatin, cladribine, colchicine, conjugated estrogens, cyclophosphamide, cyclothosphamide, cytarabine, cytarabine, cytochalasin B, cytoxan, dacarbazine, dactinomycin, dactinomycin (formerly actinomycin), daunorubicin, daunorubicin citrate, denileukin diftitox, dexrazoxane, dibromomannitol, dihydroxy anthracin dione, docetaxel, dolasetron mesylate, doxorubicin, dronabinol, E. coli L-asparaginase, eolociximab, emetine, epoetin-α, Erwinia L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine, glucocorticoids, goserelin acetate, gramicidin D, granisetron, hydroxyurea, idarubicin, ifosfamide, interferon α-2b, irinotecan, letrozole, leucovorin calcium, leuprolide acetate, levamisole, lidocaine, lomustine, maytansinoid, mechlorethamine, medroxyprogesterone acetate, megestrol acetate, melphalan, mercaptopurine, mesna, methotrexate, methyltestosterone, mithramycin, mitomycin C, mitotane, mitoxantrone, nilutamide, octreotide acetate, ondansetron, paclitaxel, pamidronate disodium, pentostatin, pilocarpine, plimycin, polifeprosan 20 with carmustine implant, porfimer sodium, procaine, procarbazine, propranolol, rituximab, sargramostim, streptozotocin, tamoxifen, taxol, teniposide, tenoposide, testolactone, tetracaine, thioepa chlorambucil, thioguanine, thiotepa, topotecan, toremifene citrate, trastuzumab, tretinoin, valrubicin, vinblastine sulfate, vincristine sulfate, and vinorelbine tartrate, or any salt thereof. In some embodiments, the methods comprise administering at least one chemotherapeutic agent to the patient.

Any anti-angiogenic agent can be used in conjunction with the antibodies, or antigen-binding fragments thereof, described herein. In some embodiments, the anti-angiogenic agent is a VEGF antagonist or another VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternately, or in addition, an anti-VEGF antibody may be co-administered to the patient.

The therapeutic regimen administered to the patient can vary depending on the patient' age, weight, and disease condition. The therapeutic regimen can continue for 2 weeks to indefinitely. In some embodiments, the therapeutic regimen is continued for about 2 weeks to about 6 months, from about 3 months to about 5 years, from about 6 months to about 1 or about 2 years, from about 8 months to about 18 months, or the like. The therapeutic regimen can be a non-variable dose regimen or a multiple-variable dose regimen.

The amount of the antibodies, or antigen-binding fragments thereof, described herein administered can depend upon a variety of factors including, but not limited to, the particular type of solid tumor treated, the stage of the solid tumor being treated, the mode of administration, the frequency of administration, the desired therapeutic benefit, and other parameters such as the age, weight and other characteristics of the patient. Determination of dosages effective to provide therapeutic benefit for specific modes and frequency of administration is within the capabilities of those skilled in the art. Dosages effective to provide therapeutic benefit may be estimated initially from in vivo animal models or clinical trials. Suitable animal models for a wide variety of diseases are known in the art. The antibodies, or antigen-binding fragments thereof, described herein may be administered by any route appropriate to the condition to be treated.

In some embodiments, the antibodies, or antigen-binding fragments thereof, described herein are provided as a lyophilized powder in a vial. The vials can contain about 100 mg, about 125 mg, about 150 mg, about 200 mg, about 250 mg, about 300 mg, or about 400 mg of the antibodies, or antigen-binding fragments thereof. Prior to administration, the lyophilized powder can be reconstituted with sterile water for injection (SWFI) or other suitable medium to provide a solution containing the antibodies, or antigen-binding fragments thereof, described herein. In some embodiments, the resulting reconstituted solution is further diluted with saline or other suitable medium for infusion and administered via, for example, an IV infusion twice every 7 days, once every 7 days, once every 14 days, once every 21 days, once every 28 days, once every 35 days, once every 42 days, once every 49 days, or once every 56 days. In some embodiments, for the first cycle, the infusion occurs over 90 minutes. In some embodiments, subsequent infusions are over 60 minutes.

In some embodiments, the antibodies, or antigen-binding fragments thereof, described herein are administered as an IV infusion once every 7 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the antibodies, or antigen-binding fragments thereof, described herein are administered as an IV infusion once every 14 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the antibodies, or antigen-binding fragments thereof, described herein are administered as an IV infusion once every 21 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the antibodies, or antigen-binding fragments thereof, described herein are administered as an IV infusion once every 28 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg.

When administered adjunctive to or with other agents, such as other chemotherapeutic agents, the antibodies, or antigen-binding fragments thereof, described herein can be administered on the same schedule as the other agent(s), or on a different schedule. When administered on the same schedule, the antibodies, or antigen-binding fragments thereof, described herein can be administered before, after, or concurrently with the other agent. In some embodiments, where the antibodies, or antigen-binding fragments thereof, described herein are administered adjunctive to, or with, standards of care, the antibodies, or antigen-binding fragments thereof, can be initiated prior to commencement of the standard therapy, for example one day, several days, one week, several weeks, one month, or even several months before commencement of standard of care therapy. In some embodiments, where the antibodies, or antigen-binding fragments thereof, described herein are administered adjunctive to, or with, standards of care, the antibodies, or antigen-binding fragments thereof, described herein can be initiated after commencement of the standard therapy, for example one day, several days, one week, several weeks, one month, or even several months after commencement of standard of care therapy.

The dosing schedule for subcutaneous administration can vary from once every six months to daily depending on a number of clinical factors, including the type of disease, severity of disease, and the patient's sensitivity to the antibodies, or antigen-binding fragments thereof, described herein.

The present disclosure also provides methods of treating Posterior Capsule Opacification (PCO), the methods comprising administering to a human patient in need thereof the antibodies, or antigen-binding fragments thereof, described herein. In some embodiments, the antibodies, or antigen-binding fragments thereof, are administered to the eye.

The present disclosure also provides methods of treating fibrosis, the methods comprising administering to a human patient in need thereof the antibodies, or antigen-binding fragments thereof, described herein. In some embodiments, the antibodies, or antigen-binding fragments thereof, are administered to an organ. In some embodiments, the organ is a kidney or lung.

In some embodiments, the antibodies, or antigen-binding fragments thereof, described herein can be used in methods of isolating and/or purifying cells, such as, for example, myofibroblast progenitors, by sorting cells that bind thereto. Such cells can rapidly migrate to wounds in the skin, lens, retina, and brain, thereby aiding in wound healing. Such cells have the potential to develop into contractile myofibroblasts. Human adipose tissue is one source of such cells (i.e., BAI1$^+$ cells) (unpublished result). Isolated BAI1$^+$ cells can be administered to a human or implanted into slowly healing or non-healing wounds, such as diabetic and decubitis ulcers and severe surgical resections, to facilitate wound closure.

In some embodiments, the antibodies, or antigen-binding fragments thereof, described herein can be used in methods of isolating neuroprotective cells by sorting cells that bind thereto. Cells that express BAI1 increase in number in response to injury of the retina and brain. Such cells can be administered to the retina and brain to reduce the death of neurons. BAI1$^+$ cells and/or the molecule(s) they produce can be injected into the vitreous of the eye or vasculature of the brain following injury.

The following representative embodiments are presented:

Embodiment 1. An antibody, or antigen-binding fragment thereof, that binds to human Adhesion G Protein-Coupled Receptor B1 (BAI1) protein, wherein the antibody, or antigen-binding fragment thereof, comprises: a first complementarily determining region (CDR) in the variable heavy ($V_H$) chain ($V_H$-CDR1) comprising an amino acid sequence according to SEQ ID NO:7; a second CDR in the $V_H$ chain ($V_H$-CDR2) comprising an amino acid sequence according to SEQ ID NO:8; a third CDR in the $V_H$ chain ($V_H$-CDR3) comprising an amino acid sequence according to SEQ ID NO:9; a first CDR in the variable light ($V_L$) chain ($V_L$-CDR1) comprising an amino acid sequence according to SEQ ID NO:10; a second CDR in the $V_L$ chain ($V_L$-CDR2) comprising an amino acid sequence according to SEQ ID NO:11; and a third CDR in the $V_L$ chain ($V_L$-CDR3) comprising an amino acid sequence according to SEQ ID NO:12.

Embodiment 2. The antibody, or antigen-binding fragment thereof, according to embodiment 1, wherein the antibody, or antigen-binding fragment thereof, comprises a $V_H$ chain comprising an amino acid sequence according to SEQ ID NO:1.

Embodiment 3. The antibody, or antigen-binding fragment thereof, according to embodiment 1, wherein the antibody, or antigen-binding fragment thereof, comprises a $V_L$ chain comprising an amino acid sequence according to SEQ ID NO:4.

Embodiment 4. The antibody, or antigen-binding fragment thereof, according to embodiment 1, wherein the antibody, or antigen-binding fragment thereof, comprises a $V_H$ chain comprising an amino acid sequence according to SEQ ID NO:1 and a $V_L$ chain comprising an amino acid sequence according to SEQ ID NO:4.

Embodiment 5. The antibody, or antigen-binding fragment thereof, according to any one of embodiments 1 to 4, wherein the antibody is an IgM or IgG antibody.

Embodiment 6. The antibody, or antigen-binding fragment thereof, according to any one of embodiments 1 to 4, wherein the antibody is an IgM antibody.

Embodiment 7. The antibody, or antigen-binding fragment thereof, according to any one of embodiments 1 to 4, wherein the antibody is an IgG antibody.

Embodiment 8. The antibody, or antigen-binding fragment thereof, according to embodiment 7, wherein the antibody is an IgG1 antibody.

Embodiment 9. The antibody, or antigen-binding fragment thereof, according to embodiment 7, wherein the antibody is an IgG1 G1m17 allotype antibody.

Embodiment 10. The antibody, or antigen-binding fragment thereof, according to any one of embodiments 1 to 9, wherein the antibody, or antigen-binding fragment thereof, is humanized.

Embodiment 11. The humanized antibody, or antigen-binding fragment thereof, according to embodiment 10, wherein the humanized antibody, or antigen-binding fragment thereof, comprises a heavy chain comprising an amino acid sequence according to SEQ ID NO:13.

Embodiment 12. The humanized antibody, or antigen-binding fragment thereof, according to embodiment 10, wherein the humanized antibody, or antigen-binding fragment thereof, comprises a light chain comprising an amino acid sequence according to SEQ ID NO:14.

Embodiment 13. The humanized antibody, or antigen-binding fragment thereof, according to embodiment 10, wherein the humanized antibody, or antigen-binding fragment thereof, comprises a heavy chain comprising an amino acid sequence according to SEQ ID NO:13 and a light chain comprising an amino acid sequence according to SEQ ID NO:14.

Embodiment 14. The antibody, or antigen-binding fragment thereof, according to any one of embodiments 1 to 13, wherein the antibody, or antigen-binding fragment thereof, is conjugated to an effector moiety.

Embodiment 15. The antibody, or antigen-binding fragment thereof, according to embodiment 14, wherein the effector moiety is a detectable label, a cytotoxic agent, a chemotherapeutic agent, or a nucleic acid molecule.

Embodiment 16. The antibody, or antigen-binding fragment thereof, according to embodiment 15, wherein the detectable label is radioactive compound, a fluorescent compound, a chromophore, an enzyme, an imaging agent, a metal ion, or a substrate.

Embodiment 17. The antibody, or antigen-binding fragment thereof, according to embodiment 15, wherein the cytotoxic agent is a small molecule, a prodrug, a maytansinoid, or a toxin.

Embodiment 18. The antibody, or antigen-binding fragment thereof, according to embodiment 15, wherein the antibody, or antigen-binding fragment thereof, comprises from 3 to 5 maytansinoid molecules per antibody, or antigen-binding fragment thereof.

Embodiment 19. The antibody, or antigen-binding fragment thereof, according to embodiment 18, wherein the maytansinoid is conjugated to the antibody, or antigen-binding fragment thereof, by a chemical linker chosen from N-succinimidyl-3-(2-pyridyldithio) propionate, N-succinimidyl-4-(2-pyridylthio)pentanoate (SPP), and succinimidyl-4-(N-maleimidomethyl)cyclohexanal-1-carboxylate.

Embodiment 20. The antibody, or antigen-binding fragment thereof, according to embodiment 15, wherein the cytotoxic agent is taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, or puromycin.

Embodiment 21. The antibody, or antigen-binding fragment thereof, according to embodiment 15, wherein the chemotherapeutic agent is cisplatin, carboplatin, oxaliplatin, nedaplatin, triplatin tetranitrate, phenanthriplatin, picoplatin, satraplatin, methotrexate, vincristine, doxorubicin, tunicamycin, oligomycin, bortezomib, MG132, 5-flurouracil, sorafenib, flavopiridol, gemcitabine, taxol, mercaptopurine, thioguanine, hydroxyurea, cytarabine, mitomycin, cyclophosphamide, ifosfamide, nitrosourea, dacarbazine, procarbazine, an etoposide, a campathecin, bleomycin, idarubicin, daunorubicin, dactinomycin, distamycin A, ethidium, netropsin, auristatin, amsacrine, prodigiosin, bortezomib, pibenzimol, togamycin, duocarmycin SA, plicamycin, mitoxantrone, asparaginase, vinblastine, vinorelbine, paclitaxel, docetaxel, CPT-11, gleevec, erlotinib, gefitinib, ibrutinib, crizotinib, ceritinib, lapatinib, navitoclax, or regorafenib.

Embodiment 22. The antibody, or antigen-binding fragment thereof, according to embodiment 15, wherein the nucleic acid molecule is a single layer nucleic acid carrier, a 1.5 layer nucleic acid carrier, a two layer nucleic acid carrier, a 2.5 layer nucleic acid carrier, or a three layer nucleic acid carrier.

Embodiment 23. The antibody, or antigen-binding fragment thereof, according to any one of embodiments 1 to 22, wherein the antigen-binding fragment is an Fab, an F(ab')2, an Fv, an scFv, an scFv-Fc, a diabody, or a minibody fragment.

Embodiment 24. A pharmaceutical composition comprising the antibody, or antigen-binding fragment thereof, according to any one of embodiments 1 to 23 and a pharmaceutically acceptable carrier.

Embodiment 25. The pharmaceutical composition according to embodiment 24, wherein the pharmaceutical composition is a liquid pharmaceutical composition.

Embodiment 26. The pharmaceutical composition according to embodiment 24 or embodiment 25, further comprising a tonicity agent, a surfactant, a preservative, and/or a buffer system having a pH of about 4.0 to about 8.0.

Embodiment 27. An isolated nucleic acid molecule encoding the $V_H$ chain of the antibody, or antigen-binding fragment thereof, according to any one of embodiments 1 to 9, wherein the nucleic acid molecule comprises a nucleotide sequence according to SEQ ID NO:2 or SEQ ID NO:3.

Embodiment 28. An isolated nucleic acid molecule encoding the $V_L$ chain of the antibody, or antigen-binding fragment thereof, according to any one of embodiments 1 to 9, wherein the nucleic acid molecule comprises a nucleotide sequence according to SEQ ID NO:5 or SEQ ID NO:6.

Embodiment 29. A vector comprising the nucleic acid molecule according to embodiment 27 or embodiment 28.

Embodiment 30. A prokaryotic host cell transformed with the vector according to embodiment 29.

Embodiment 31. A eukaryotic host cell transformed with the vector according to embodiment 29.

Embodiment 32. The eukaryotic host cell according to embodiment 31 which is a mammalian host cell.

Embodiment 33. A method of detecting a cell expressing BAI1, the method comprising contacting the cell with the antibody, or antigen-binding fragment thereof, according to any one of embodiments 1 to 23, and detecting the antibody, or antigen-binding fragment thereof.

Embodiment 34. The method according to embodiment 33, wherein the cell is present in a biological sample obtained from a human and the cell is contacted with the antibody, or antigen-binding fragment thereof, in vitro.

Embodiment 35. The method according to embodiment 33, wherein the cell is present in a human and the cell is contacted with the antibody, or antigen-binding fragment thereof, in vivo.

Embodiment 36. A method of treating a cancer expressing BAI1, the method comprising administering to a human patient in need thereof the antibody, or antigen-binding fragment thereof, according to any one of embodiments 1 to 23.

Embodiment 37. The method according to embodiment 36, wherein the BAI1 expressing cancer is a neurological cancer.

Embodiment 38. The method according to embodiment 37, wherein the neurological cancer is a primary brain tumor, a glioblastoma, a glioma, a meningioma, a neurinoma, a pituitary adenoma, a medulloblastoma, a craniopharyngioma, a hemangioma, an epidermoid, a sarcoma, or an intracranial metastasis from other tumor sources.

Embodiment 39. The method according to embodiment 38, wherein the neurological cancer is a glioblastoma.

Embodiment 40. The method according to any one of embodiments 36 to 39, wherein the antibody, or antigen-binding fragment thereof, is administered intravenously or intracranially.

Embodiment 41. The method according to any one of embodiments 36 to 40, further comprising administering at least one chemotherapeutic agent to the patient.

Embodiment 42. The method according to any one of embodiments 36 to 41, further comprising one or both of surgically resecting tumor cells and/or administering radiation therapy.

Embodiment 43. A method of treating Posterior Capsule Opacification (PCO), the method comprising administering to a human patient in need thereof the antibody, or antigen-binding fragment thereof, according to any one of embodiments 1 to 23.

Embodiment 44. The method according to embodiment 43, wherein the antibody, or antigen-binding fragment thereof, is administered to the eye.

Embodiment 45. A method of treating fibrosis, the method comprising administering to a human patient in need thereof the antibody, or antigen-binding fragment thereof, according to any one of embodiments 1 to 23.

Embodiment 46. The method according to embodiment 45, wherein the antibody, or antigen-binding fragment thereof, is administered to an organ.

Embodiment 47. The method according to embodiment 46, wherein the organ is a kidney or lung.

Embodiment 48. A method of promoting wound healing, the method comprising administering to a human patient in need thereof the antibody, or antigen-binding fragment thereof, according to any one of embodiments 1 to 23.

Embodiment 49. The method according to embodiment 48, wherein the wound is present in the skin, eye lens, retina, or brain.

Embodiment 50. The method according to embodiment 48, wherein the wound is a diabetic ulcer or decubitis ulcer.

Embodiment 51. A method of promoting wound healing, the method comprising administering to a human patient in need thereof a cell expressing BAI1.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted. As used herein, numbering of immunoglobulin amino acid residues is carried out according to the immunoglobulin amino acid residue numbering system of Kabat et al., unless otherwise indicated.

EXAMPLES

Example 1: Identification of the G8 (BAI1) Antigen

The Membrane Proteome Array (MPA) is a platform for profiling the specificity of antibodies and other ligands that target human membrane proteins. The MPA can be used to determine antibody target specificity, deconvolute orphan antibody targets, and characterize the target profile of biosimilar candidates. Flow cytometry is used to directly detect antibody binding to membrane proteins expressed in eukaryotic cells, such as human HEK-293 cells. Consequently, all MPA targets are designed to have native conformations and the appropriate post-translational modifications. The workflow of the process is shown in FIG. 1. G8 antibody was tested for reactivity against the MPA library of over 4,500 human membrane proteins, including GPCRs, ion channels, and transporters. Identified targets were validated in secondary screens to confirm reactivity.

Figure 2A:
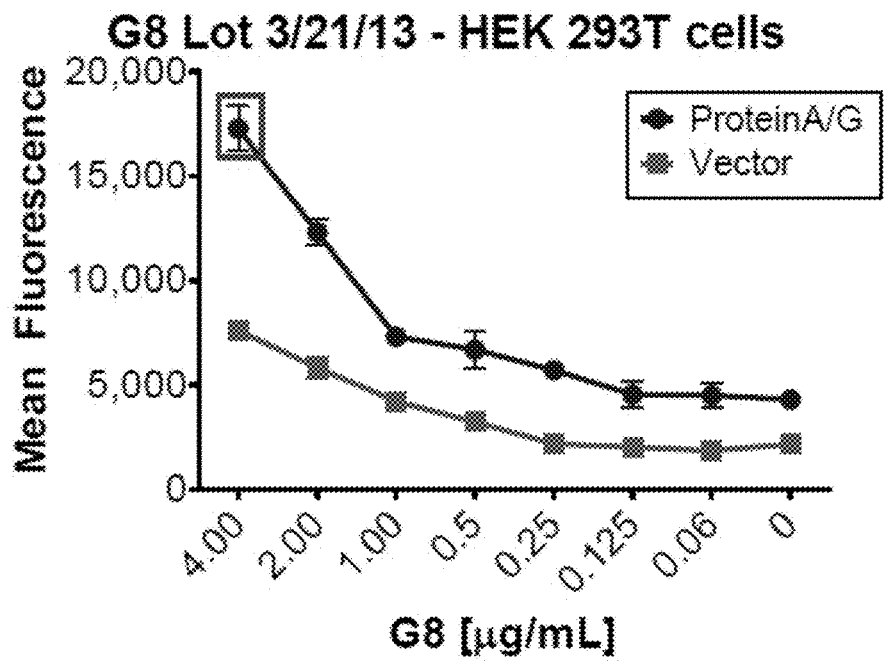
FIG. 2A shows immunodetection optimization of G8 Lot 3/21/13 in HEK-293T cells. Each point represents the average of four replicates. The recommended working concentration for screening each antibody based on signal to background (S/B) calculations and raw signal values is highlighted in red.
Figure 2B:
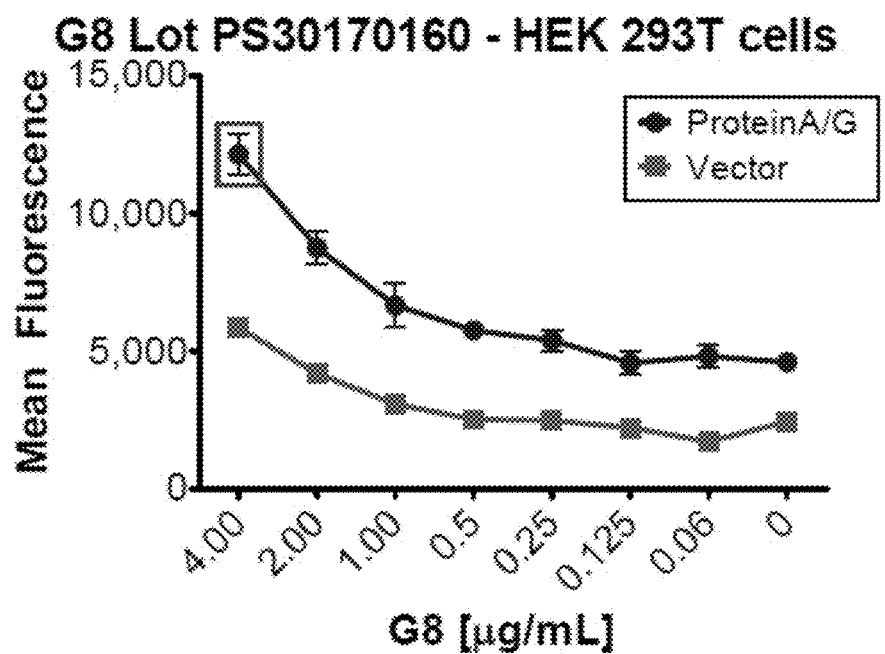
FIG. 2B shows immunodetection optimization of G8 Lot PS30170160 in HEK-293T cells. Each point represents the average of four replicates. The recommended working concentration for screening each antibody based on signal to background (S/B) calculations and raw signal values is highlighted in red.

To determine the optimal antibody concentration and minimize background reactivity, different concentrations of G8 Lot 3/21/13 and G8 Lot PS30170160 were examined using HEK-293T (human) cells expressing either Protein A and Protein G constructs or vector alone. These experiments were conducted in a 384-well format using a single dilution of secondary antibody (FIGS. 2A and 2B; Table 1). Data from the assay setup experiments was used to determine the optimal screening conditions for high-throughput immunodetection (Table 2). In brief, to optimize conditions for antibody detection, cells were transfected with Protein A and G expression constructs (positive control for MAb binding) or vector alone (negative control) in 384-well format, followed by detection of cellular expression using a high-throughput immunofluorescence flow cytometry assay. Serial dilutions of each test and control MAb (beginning with 4 μg/ml) were examined for immunoreactivity against cells expressing the Protein A and G or vector alone. It was discovered that IgM does not react strongly with positive control constructs. As a result, these experiments were used to determine conditions that showed low background reactivity. Low background reactivity indicates that detection at high concentrations is possible without masking a potential hit.

TABLE 1

Screening conditions

| [MAb] μg/mL | G8 Lot 3/21/13 | | G8 Lot PS30170160 | |
|---|---|---|---|---|
| | Signal | Background MFI | Signal | Background MFI |
| 4 | 17,277 | 7,613 | 12,143 | 5,851 |
| 2 | 12,315 | 5,841 | 8,754 | 4,193 |
| 1 | 7,312 | 4,232 | 6,663 | 3,076 |
| 0.5 | 6,700 | 3,244 | 5,753 | 2,532 |
| 0.25 | 5,713 | 2,193 | 5,393 | 2,489 |
| 0.13 | 5,554 | 2,036 | 4,581 | 2,227 |
| 0.06 | 4,519 | 1,868 | 4,812 | 1,720 |
| 0.03 | 4,317 | 2,168 | 4,605 | 2,445 |

TABLE 2

Experimental Parameters for High-Throughput Immunodetection

| Experimental Parameter | G8 Lot 3/21/13 | G8 Lot PS30170160 |
|---|---|---|
| Cells | HEK 293T | HEK 293T |
| Blocking Buffer | 10% Goat Serum | 10% Goat Serum |
| 1° Ab | | |
| Ab Name | G8 Lot 3/21/13 | G8 Lot PS30170160 |
| Optimal Conc. Incubation (RT) | 4 μg/ml (30 μg/ml, run after 4 μg/ml yielded no hits) 60 min | 4 μg/ml (30 μg/ml, run after 4 μg/ml yielded no hits) 60 min |
| 2° Ab | | |
| Target | Mouse IgM (Fab) | Mouse IgM (Fab) |
| Optimal Conc. Incubation (RT) Manufacturer Cat # Antibody ID | 1:100 (15 μg/ml) 30 min Jackson ImmunoResearch 115-546-020 AlexaFluor ® 488-AffiniPure Goat Fab Anti-Mouse IgM (Fc) | 1:100 (15 μg/ml) 30 min Jackson ImmunoResearch 115-546-020 AlexaFluor ® 488-AffiniPure Goat Fab Anti-Mouse IgM (Fc) |
| Washes | PBS (without $Ca^{2+}$, $Mg^{2+}$) | PBS (without $Ca^{2+}$, $Mg^{2+}$) |

Determination of Antibody Binding Targets

Figure 3A:
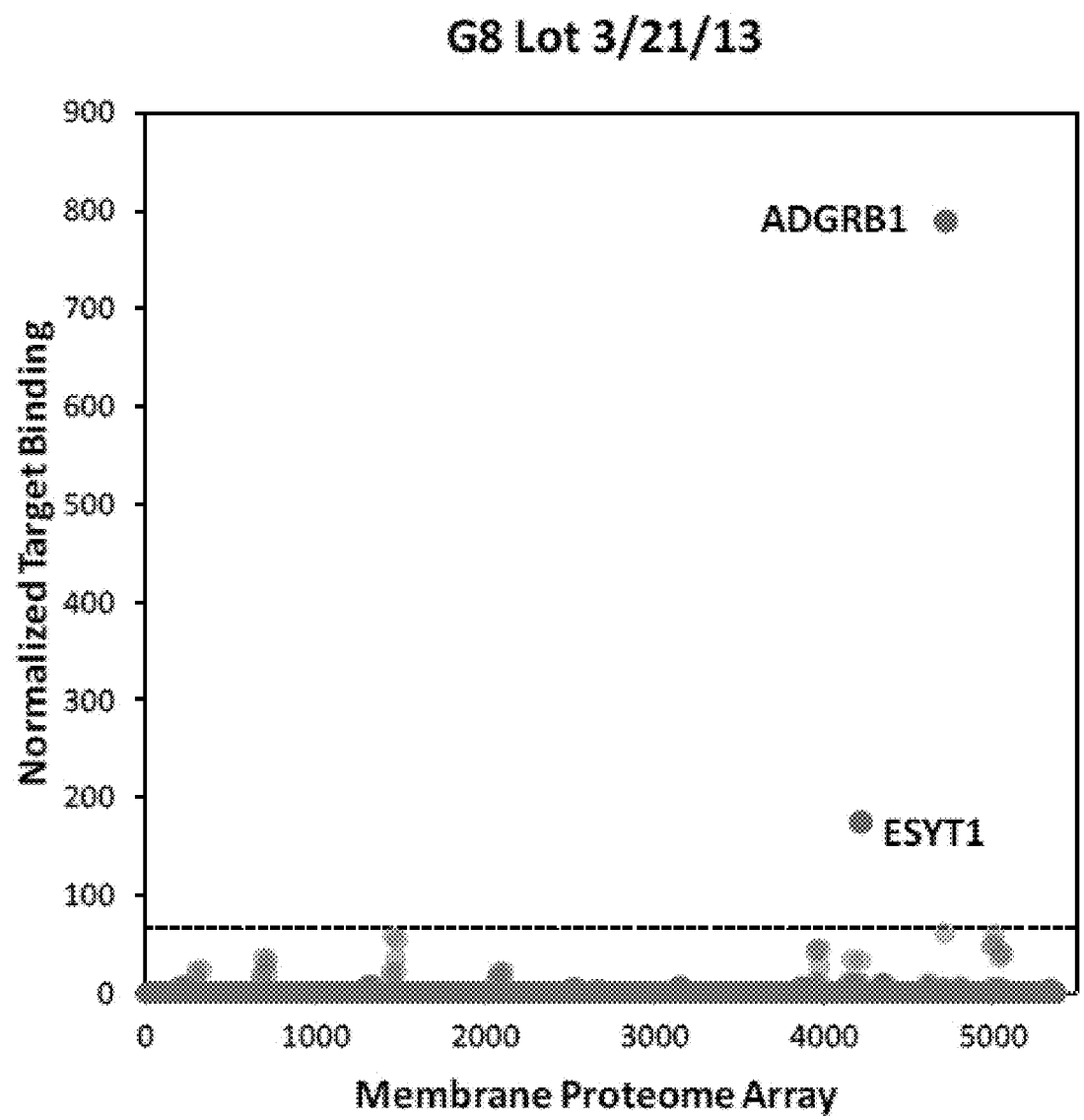
FIG. 3A shows identification of membrane protein binding targets for G8 Lot 3/21/13. Non-specific fluorescence was determined to be any value below 3 standard deviations above noise (dotted line). The targets that showed increased antibody binding are displayed above the dotted line and denoted in red.
Figure 3B:
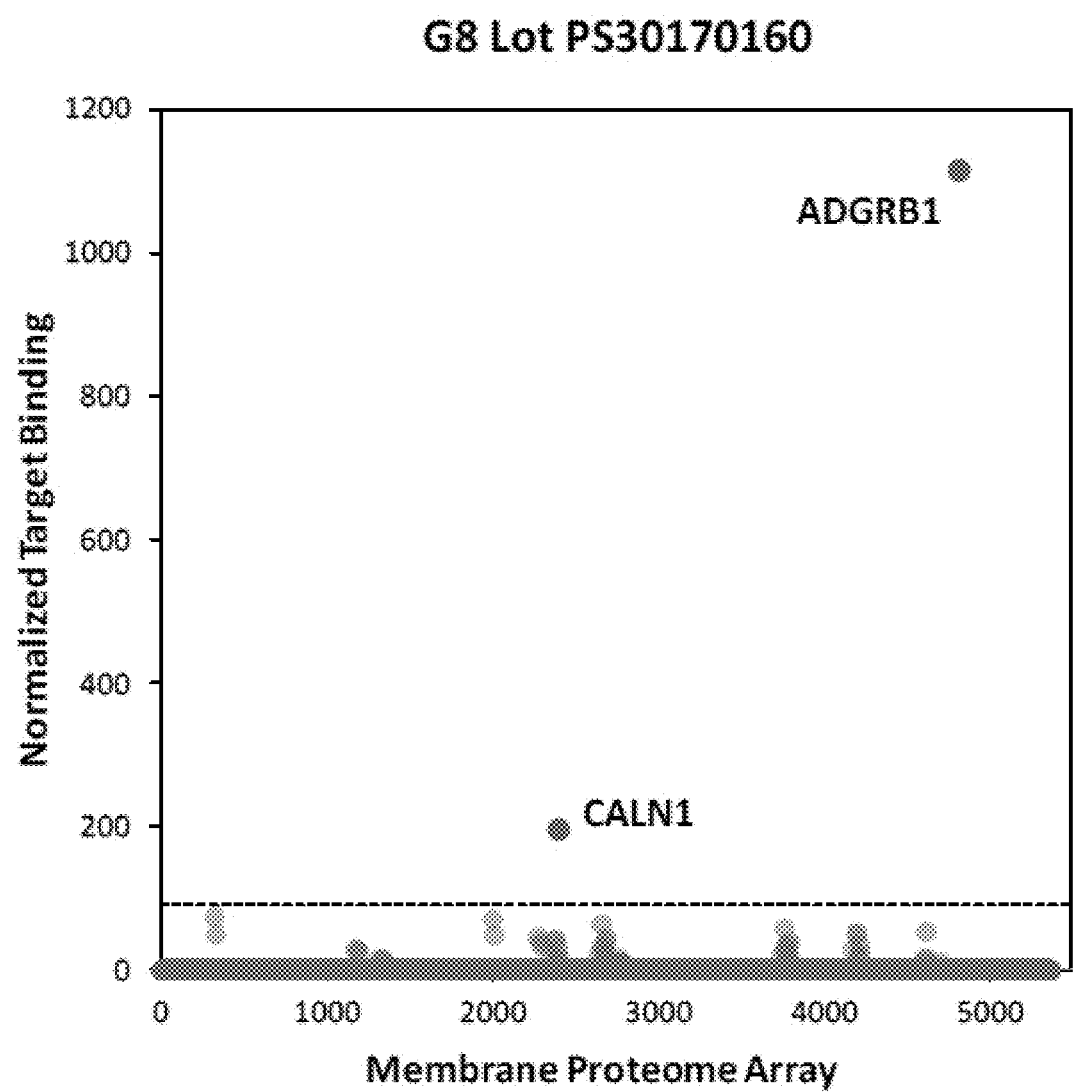
FIG. 3B shows identification of membrane protein binding targets for G8 Lot PS30170160. Non-specific fluorescence was determined to be any value below 3 standard deviations above noise (dotted line). The targets that showed increased antibody binding are displayed above the dotted line and denoted in red.

To identify antibody binding targets, 5,300 different membrane proteins were each expressed in individual wells of HEK-293T cells arrayed in 384-well plates. The cells were then matrixed by pooling individual columns and rows of each 384-well plate. The resulting MPA matrix was probed with G8 Lot 3/21/13 and G8 Lot PS30170160 at concentrations of 30 µg/ml followed by detection using a fluorescently-labeled secondary antibody. Fluorescence readings from each experimental plate were validated using positive (construct expressing Known Target) and negative (empty vector) controls. Each individual membrane protein target was assigned values corresponding to the binding values of their unique row and column pools. The resulting binding values (comprising row and column components) were normalized and transformed to give a single numerical value for binding of the antibody against each target protein (Normalized Target Binding). Targets were then identified by detecting antibody binding to overlapping column and row pools emanating from the same plate, thereby allowing specific deconvolution (FIGS. 3A and 3B; Table 3). Antibody binding was detected by flow cytometry using a fluorescent secondary antibody.

TABLE 3

G8 Lot: 3/21/13 and Lot: PS30170160 Membrane Protein Targets

| Antibody | Target gene (HGNC) | Uniprot |
|---|---|---|
| G8 Lot 3/21/13 | BAI1 | E5RG74 |
| G8 Lot PS30170160 | BAI1 | E5RG74 |

Figure 4A:
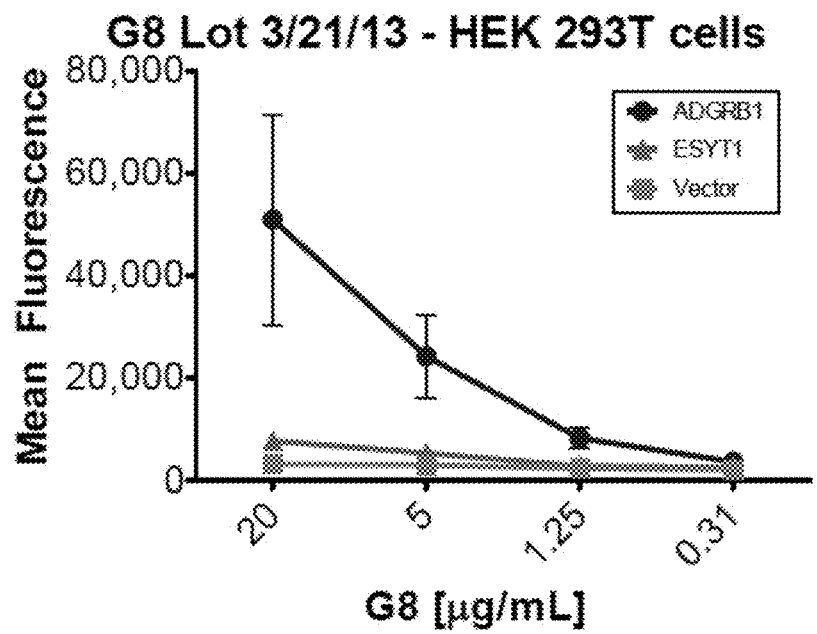
FIG. 4A shows validation of binding for G8 Lot 3/21/13. Each point represents the average of four replicates.
Figure 4B:
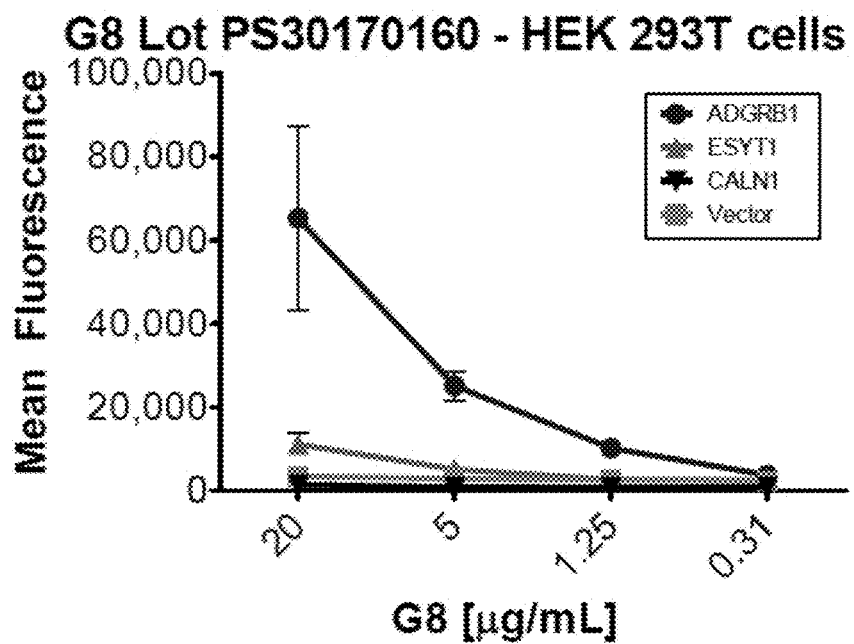
FIG. 4B shows validation of binding for G8 Lot PS30170160. Each point represents the average of four replicates.

The screen produced binding targets that were confirmed in a second flow cytometry assay using serial antibody dilutions (FIGS. 4A and 4B). To that end, HEK-293T cells were transfected with the plasmid construct expressing target or vector alone. Serial dilutions of each MAb were tested for immunoreactivity against cells expressing the target protein or vector alone. Finally, the identity of all targets was re-verified by sequencing.

Example 2: RACE Identification of G8 Heavy and Light Chains

Figure 5:
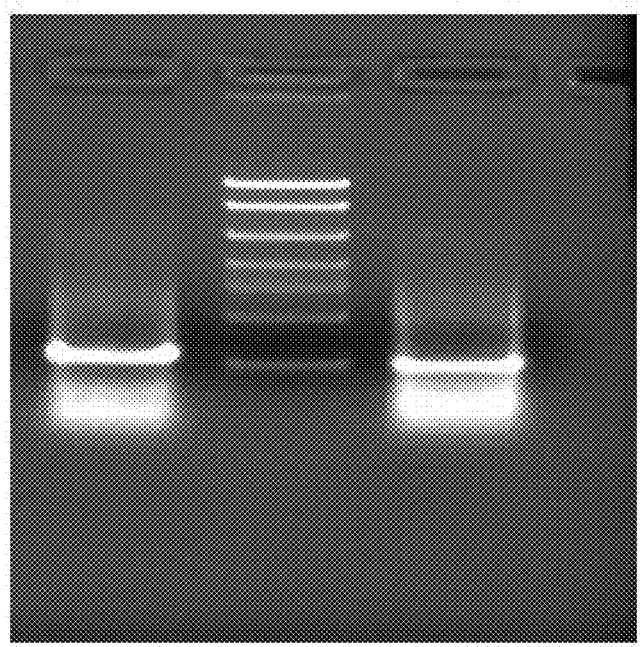
FIG. 5 shows the results of the RACE identification of heavy and light chains of mouse G8 IgM.

To identify the nucleic acid molecule encoding heavy and light chains of the G8 antibody, a Rapid Amplification of cDNA Ends (RACE) reaction was conducted. The RACE PCR reaction samples were analyzed on an agarose gel to visualize the amplified DNA fragments. The correct antibody variable region DNA fragments having a size between 500-700 base pairs were amplified (FIG. 5).

The PCR-amplified DNA fragments from 24 clones were recovered from agarose gels, and sequenced. The CDRs were identified using the VBASE2 tool.

Example 3: Construction, Production and Characterization of Humanized Anti-BAH IgG The expression constructs of G8 IgG were cloned into a high expression mammalian vector. Each DNA construct of G8 IgG was scaled up for transfection and sequences were confirmed. A 0.03 liter transient production was completed in HEK293 cells (Tuna293™ Process). The conditioned media from the transient production run was harvested and clarified by centrifugation and filtration. The supernatant was loaded over a Protein A column pre-equilibrated with binding buffer. Washing buffer was passed through the column until the $OD_{280}$ value (NanoDrop, Thermo Scientific) was measured to be zero. The target protein was eluted with a low pH buffer, fractions were collected, and the $OD_{280}$ value of each fraction was recorded. Fractions containing the target protein were pooled and filtered through a 0.2 µm membrane filter. The protein concentration was calculated from the $OD_{280}$ value and the calculated extinction coefficient, and 2.92 mg of G8 IgG was obtained. The data is summarized in Table 4. Final protein yields, aliquots and analysis.

TABLE 4

| Protein name | Lot # | Internal HC# | HC Details | Internal LC# | LC Details | Conc. (mg/mL) |
|---|---|---|---|---|---|---|
| G8 IgG | 14163-819774 | H7873 | hIgG1 (G1m17) | L7873 | hKappa | 0.73 |

| Protein name | Lot # | Vol. (mL) | No. of vials | Total Yield (mg) | Endotoxin (EU/mg) |
|---|---|---|---|---|---|
| G8 IgG | 14163-819774 | 1 | 4 | 2.92 | <1 |

Subsequently, CE-SDS analysis was performed was performed using LabChip GXII (Perkin Elmer). Endotoxin measurements were run on a sample of the purified product using the chromogenic Limulus Amebocyte Lysate method (Endosafe-MCS, Charles River). The sample was run in duplicate. The experiments confirmed all samples met <1 EU/mg requirement (Table 4). SE-UPLC analysis was performed wherein SEC standard (MEDNA, Cat No. Y3101) were run as a reference for protein size. All proteins were observed to contain >99% monomers. Intact Mass QC by Mass Spec was performed and the observed molecular weight for the IgG was within the expected range.

Figure 6:
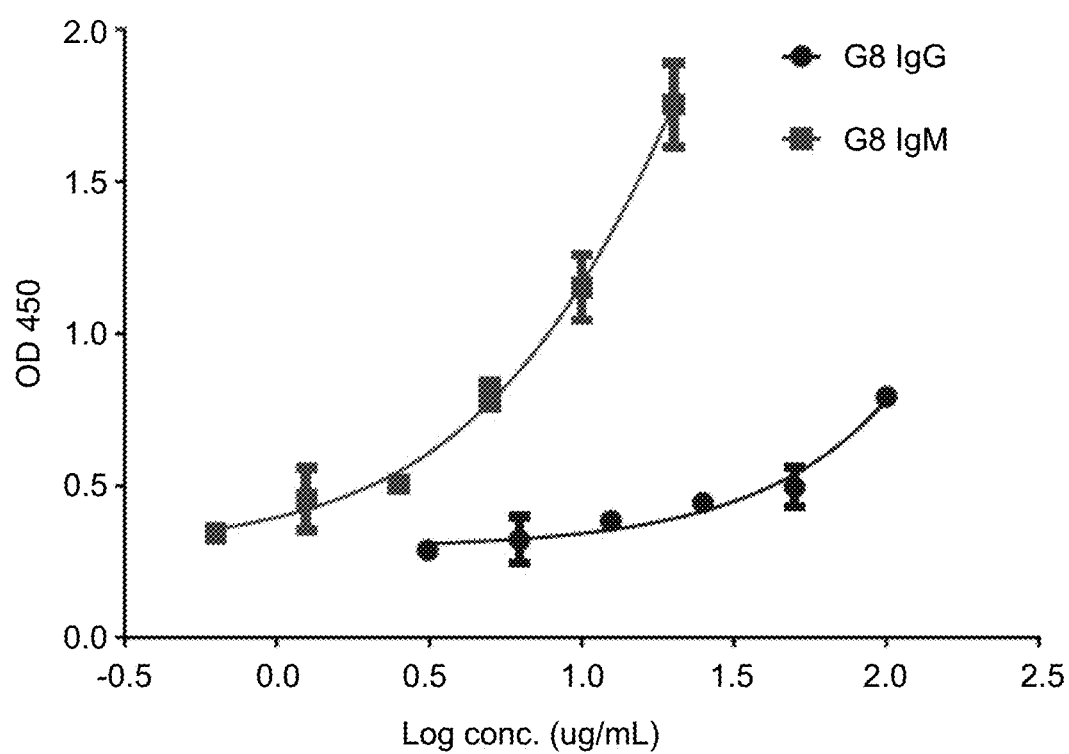
FIG. 6 shows the results of the ELISA assay of G8 IgM (boxes) and anti-BAI1 IgG (circles; also designated herein as "G8 IgG").

To measure the relative affinities of G8 IgM and anti-BAI1 IgG (also designated herein as "G8 IgG") an ELISA assay was performed and both G8 IgG and G8 IgM. Briefly, the plate was coated with 2 µg/ml human BAI1 overnight at 4° C., blocked with 1% BSA in PBS for 1 hour at room temperature. The primary incubation was carried out for 1 hour at room temperature with either serial 1:2 dilutions of G8 IgM, starting at 20 µg/ml or serial 1:2 dilutions of G8 IgG (anti-BAI1 IgG), starting at 100 µg/ml. The secondary incubation was carried out for 1 hour at room temperature with either HRP-conjugated anti-mouse IgM Fc (G8 IgM) or HRP-conjugated anti-human Fc (G8 IgG). The assay was developed via 15 minutes incubation with 3,3',5,5'-Tetramethylbenzidine (TMB) and stopped with 1 M HCl. All assays were performed in duplicate. The results are shown in FIG. 6. Both G8 IgG and G8 IgM control sample show positive signal on ELISA.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. An antibody, or antigen-binding fragment thereof, that binds to human Adhesion G Protein-Coupled Receptor B1 (BAI1) protein, wherein the antibody, or antigen-binding fragment thereof, comprises:
   a first complementarity determining region (CDR) in the variable heavy (VH) chain (VH-CDR1) comprising an amino acid sequence according to SEQ ID NO:7;
   a second CDR in the VH chain (VH-CDR2) comprising an amino acid sequence according to SEQ ID NO:8;
   a third CDR in the VH chain (VH-CDR3) comprising an amino acid sequence according to SEQ ID NO:9;
   a first CDR in the variable light (VL) chain (VL-CDR1) comprising an amino acid sequence according to SEQ ID NO:10;
   a second CDR in the VL chain (VL-CDR2) comprising an amino acid sequence according to SEQ ID NO:11; and
   a third CDR in the VL chain (VL-CDR3) comprising an amino acid sequence according to SEQ ID NO:12.

2. The antibody, or antigen-binding fragment thereof, according to claim 1, wherein the antibody, or antigen-binding fragment thereof, comprises a VH chain comprising an amino acid sequence according to SEQ ID NO:1.

3. The antibody, or antigen-binding fragment thereof, according to claim 1, wherein the antibody, or antigen-binding fragment thereof, comprises a VL chain comprising an amino acid sequence according to SEQ ID NO:4.

4. The antibody, or antigen-binding fragment thereof, according to claim 1, wherein the antibody, or antigen-binding fragment thereof, comprises a VH chain comprising an amino acid sequence according to SEQ ID NO:1 and comprises a VL chain comprising an amino acid sequence according to SEQ ID NO:4.

5. The antibody, or antigen-binding fragment thereof, according to claim 1, wherein the antibody is an IgM or IgG antibody.

6. The antibody, or antigen-binding fragment thereof, according to claim 1, wherein the antibody, or antigen-binding fragment thereof, is humanized.

7. The humanized antibody, or antigen-binding fragment thereof, according to claim 6, wherein the humanized antibody, or antigen-binding fragment thereof, comprises a heavy chain comprising an amino acid sequence according to SEQ ID NO:13.

8. The humanized antibody, or antigen-binding fragment thereof, according to claim 6, wherein the humanized antibody, or antigen-binding fragment thereof, comprises a light chain comprising an amino acid sequence according to SEQ ID NO:14.

9. The humanized antibody, or antigen-binding fragment thereof, according to claim 6, wherein the humanized antibody, or antigen-binding fragment thereof, comprises a heavy chain comprising an amino acid sequence according to SEQ ID NO:13, and comprises a light chain comprising an amino acid sequence according to SEQ ID NO:14.

10. The antibody, or antigen-binding fragment thereof, according to claim 1, wherein the antibody, or antigen-binding fragment thereof, is conjugated to an effector moiety.

11. The antibody, or antigen-binding fragment thereof, according to claim 10, wherein the effector moiety is a detectable label, a cytotoxic agent, a chemotherapeutic agent, or a nucleic acid molecule.

12. The antibody, or antigen-binding fragment thereof, according to claim 11, wherein the antibody, or antigen-binding fragment thereof, comprises from 3 to 5 maytansinoid molecules per antibody, or antigen-binding fragment thereof.

13. The antibody, or antigen-binding fragment thereof, according to claim 11, wherein the nucleic acid molecule is a single layer nucleic acid carrier, a 1.5 layer nucleic acid carrier, a two layer nucleic acid carrier, a 2.5 layer nucleic acid carrier, or a three layer nucleic acid carrier.

14. The antibody, or antigen-binding fragment thereof, according to claim 1, wherein the antigen-binding fragment is an Fab, an F(ab')2, an Fv, an scFv, an scFv-Fc, a diabody, or a minibody fragment.

15. A pharmaceutical composition comprising the antibody, or antigen-binding fragment thereof, according to claim 1 and a pharmaceutically acceptable carrier.

16. An isolated nucleic acid molecule encoding the VH chain of the antibody, or antigen-binding fragment thereof, according to claim 1, wherein the nucleic acid molecule comprises a nucleotide sequence according to SEQ ID NO:2 or SEQ ID NO:3.

17. An isolated nucleic acid molecule encoding the VL chain of the antibody, or antigen-binding fragment thereof, according to claim 1, wherein the nucleic acid molecule comprises a nucleotide sequence according to SEQ ID NO:5 or SEQ ID NO:6.

18. A method of detecting a cell expressing BAI1, the method comprising contacting the cell with the antibody, or antigen-binding fragment thereof, according to claim 1, and detecting the antibody, or antigen-binding fragment thereof.

* * * * *

```
                        SEQUENCE LISTING

<160> NUMBER OF SEQ ID NOS: 15

<210> SEQ ID NO 1
<211> LENGTH: 118
<212> TYPE: PRT
<213> ORGANISM: homo sapien

<400> SEQUENCE: 1

Ser Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Ser Tyr Ser Gly Ser Thr Ser Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Asn Ala Gln Gly Tyr Ala Met Asp Tyr Trp Gly Gln Gly Thr
            100                 105                 110

Ser Val Thr Val Ser Ser
        115

<210> SEQ ID NO 2
<211> LENGTH: 354
<212> TYPE: DNA
<213> ORGANISM: homo sapien

<400> SEQUENCE: 2
tctgatgtgc agcttcagga gtcgggacct ggcctggtga aaccttctca gtctctgtcc        60
ctcacctgca ctgtcactgg ctactcaatc accagtgatt atgcctggaa ctggatccgg       120
cagtttccag gaaacaaact ggagtggatg ggctacataa gctacagtgg tagcactagc       180
tacaacccat ctctcaaaag tcgaatctct atcactcgag acacatccaa gaaccagttc       240
ttcctgcagt tgaattctgt gactactgag gacacagcca catattactg tgccaatgcc       300
caggggtatg ctatggacta ctggggtcaa ggaacctcag tcaccgtctc ctca             354

<210> SEQ ID NO 3
<211> LENGTH: 354
<212> TYPE: RNA
<213> ORGANISM: homo sapien

<400> SEQUENCE: 3
ucugaugugc agcuucagga gucgggaccu ggccugguga aaccuucuca gucucugucc        60
```

```
cucaccugca cugucacugg cuacucaauc accagugauu augccuggaa cuggauccgg    120
caguuuccag gaaacaaacu ggaguggaug ggcuacauaa gcuacagugg uagcacuagc    180
uacaacccau cucucaaaag ucgaaucucu aucacucgag acacauccaa gaaccaguuc    240
uuccugcagu ugaauucugu gacuacugag gacacagcca cauauuacug ugccaaugcc    300 caggggguaug cuauggacua cuggggucaa ggaaccucag ucaccgucuc cuca         354
```

```
<210> SEQ ID NO 4
<211> LENGTH: 107
<212> TYPE: PRT
<213> ORGANISM: homo sapien

<400> SEQUENCE: 4

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys
            100                 105
```

```
<210> SEQ ID NO 5
<211> LENGTH: 321
<212> TYPE: DNA
<213> ORGANISM: homo sapien

<400> SEQUENCE: 5
gacattgtga tgactcagtc tccagccacc ctgtctgtga ctccaggaga tagagtctct    60
ctttcctgca gggccagcca gagtattagc gactacttac actggtatca acaaaaatca    120
catgagtctc caaggcttct catcaaatat gcttcccaat ccatctctgg gatcccctcc    180
aggttcagtg gcagtggatc agggtcagat ttcactctca gtatcaacag tggaaccct     240 gaagatgttg gagtgtatta ctgtcaaaat ggtcacagct ttccattcac gttcggctcg    300
gggacaaagt tggaaataaa a                                              321
```

```
<210> SEQ ID NO 6
<211> LENGTH: 321
<212> TYPE: RNA
<213> ORGANISM: homo sapien

<400> SEQUENCE: 6
gacauuguga ugacucaguc uccagccacc cugucuguga cuccaggaga uagagucucu    60
cuuuccugca gggccagcca gaguauuagc gacuacuuac acugguauca acaaaaauca    120
caugagucuc caaggcuucu caucaaauau gcuucccaau ccaucucugg gaucccucc     180 agguucagug gcaguggauc agggucagau uucacucuca guaucaacag uggaaccu      240 gaagauguug gaguguauua cugucaaaau ggucacagcu uuccauucac guucggcucg    300
gggacaaagu uggaaauaaa a                                              321
```

```
<210> SEQ ID NO 7
<211> LENGTH: 8
<212> TYPE: PRT
<213> ORGANISM: homo sapien

<400> SEQUENCE: 7

Gly Tyr Ser Ile Thr Ser Asp Tyr
1               5

<210> SEQ ID NO 8
<211> LENGTH: 5
<212> TYPE: PRT
<213> ORGANISM: homo sapien

<400> SEQUENCE: 8

Ser Tyr Ser Gly Ser
1               5

<210> SEQ ID NO 9
<211> LENGTH: 8
<212> TYPE: PRT
<213> ORGANISM: homo sapien

<400> SEQUENCE: 9

Ala Gln Gly Tyr Ala Met Asp Tyr
1               5

<210> SEQ ID NO 10
<211> LENGTH: 11
<212> TYPE: PRT
<213> ORGANISM: homo sapien

<400> SEQUENCE: 10

Arg Ala Ser Gln Ser Ile Ser Asp Tyr Leu His
1               5                   10

<210> SEQ ID NO 11
<211> LENGTH: 7
<212> TYPE: PRT
<213> ORGANISM: homo sapien

<400> SEQUENCE: 11

Tyr Ala Ser Gln Ser Ile Ser
1               5

<210> SEQ ID NO 12
<211> LENGTH: 9
<212> TYPE: PRT
<213> ORGANISM: homo sapien

<400> SEQUENCE: 12

Gln Asn Gly His Ser Phe Pro Phe Thr
1               5

<210> SEQ ID NO 13
<211> LENGTH: 445
<212> TYPE: PRT
<213> ORGANISM: homo sapien

<400> SEQUENCE: 13

Val Gln Leu Gln Glu Ser Gly Pro Gly Leu Val Lys Pro Ser Gln Ser
1               5                   10                  15

Leu Ser Leu Thr Cys Thr Val Thr Gly Tyr Ser Ile Thr Ser Asp Tyr
```

-continued

```
                20                  25                  30
Ala Trp Asn Trp Ile Arg Gln Phe Pro Gly Asn Lys Leu Glu Trp Met
            35                  40                  45
Gly Tyr Ile Ser Tyr Ser Gly Ser Thr Ser Tyr Asn Pro Ser Leu Lys
        50                  55                  60
Ser Arg Ile Ser Ile Thr Arg Asp Thr Ser Lys Asn Gln Phe Phe Leu
65                  70                  75                  80
Gln Leu Asn Ser Val Thr Thr Glu Asp Thr Ala Thr Tyr Tyr Cys Ala
                85                  90                  95
Asn Ala Gln Gly Tyr Ala Met Asp Tyr Trp Gly Gln Gly Thr Ser Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445
```

<210> SEQ ID NO 14
<211> LENGTH: 214
<212> TYPE: PRT
<213> ORGANISM: homo sapien

<400> SEQUENCE: 14

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15
<211> LENGTH: 1584
<212> TYPE: PRT
<213> ORGANISM: homo sapien

<400> SEQUENCE: 15

```
Met Arg Gly Gln Ala Ala Ala Pro Gly Pro Val Trp Ile Leu Ala Pro
1               5                   10                  15

Leu Leu Leu Leu Leu Leu Leu Gly Arg Arg Ala Arg Ala Ala Ala
            20                  25                  30

Gly Ala Asp Ala Gly Pro Gly Glu Pro Cys Ala Thr Leu Val Gln
        35                  40                  45

Gly Lys Phe Phe Gly Tyr Phe Ser Ala Ala Val Phe Pro Ala Asn
50                  55                  60

Ala Ser Arg Cys Ser Trp Thr Leu Arg Asn Pro Asp Pro Arg Arg Tyr
65                  70                  75                  80

Thr Leu Tyr Met Lys Val Ala Lys Ala Pro Val Pro Cys Ser Gly Pro
                85                  90                  95

Gly Arg Val Arg Thr Tyr Gln Phe Asp Ser Phe Leu Glu Ser Thr Arg
            100                 105                 110
```

-continued

```
Thr Tyr Leu Gly Val Glu Ser Phe Asp Glu Val Leu Arg Leu Cys Asp
        115                 120                 125

Pro Ser Ala Pro Leu Ala Phe Leu Gln Ala Ser Lys Gln Phe Leu Gln
    130                 135                 140

Met Arg Arg Gln Gln Pro Pro Gln His Asp Gly Leu Arg Pro Arg Ala
145                 150                 155                 160

Gly Pro Pro Gly Pro Thr Asp Asp Phe Ser Val Glu Tyr Leu Val Val
                165                 170                 175

Gly Asn Arg Asn Pro Ser Arg Ala Ala Cys Gln Met Leu Cys Arg Trp
            180                 185                 190

Leu Asp Ala Cys Leu Ala Gly Ser Arg Ser His Pro Cys Gly Ile
        195                 200                 205

Met Gln Thr Pro Cys Ala Cys Leu Gly Gly Glu Ala Gly Pro Ala
    210                 215                 220

Ala Gly Pro Leu Ala Pro Arg Gly Asp Val Cys Leu Arg Asp Ala Val
225                 230                 235                 240

Ala Gly Gly Pro Glu Asn Cys Leu Thr Ser Leu Thr Gln Asp Arg Gly
                245                 250                 255

Gly His Gly Ala Thr Gly Gly Trp Lys Leu Trp Ser Leu Trp Gly Glu
            260                 265                 270

Cys Thr Arg Asp Cys Gly Gly Gly Leu Gln Thr Arg Thr Arg Thr Cys
        275                 280                 285

Leu Pro Ala Pro Gly Val Glu Gly Gly Gly Cys Glu Gly Val Leu Glu
    290                 295                 300

Glu Gly Arg Gln Cys Asn Arg Glu Ala Cys Gly Pro Ala Gly Arg Thr
305                 310                 315                 320

Ser Ser Arg Ser Gln Ser Leu Arg Ser Thr Asp Ala Arg Arg Glu
                325                 330                 335

Glu Leu Gly Asp Glu Leu Gln Gln Phe Gly Phe Pro Ala Pro Gln Thr
            340                 345                 350

Gly Asp Pro Ala Ala Glu Glu Trp Ser Pro Trp Ser Val Cys Ser Ser
        355                 360                 365

Thr Cys Gly Glu Gly Trp Gln Thr Arg Thr Arg Phe Cys Val Ser Ser
    370                 375                 380

Ser Tyr Ser Thr Gln Cys Ser Gly Pro Leu Arg Glu Gln Arg Leu Cys
385                 390                 395                 400

Asn Asn Ser Ala Val Cys Pro Val His Gly Ala Trp Asp Glu Trp Ser
                405                 410                 415

Pro Trp Ser Leu Cys Ser Ser Thr Cys Gly Arg Gly Phe Arg Asp Arg
            420                 425                 430

Thr Arg Thr Cys Arg Pro Pro Gln Phe Gly Gly Asn Pro Cys Glu Gly
        435                 440                 445

Pro Glu Lys Gln Thr Lys Phe Cys Asn Ile Ala Leu Cys Pro Gly Arg
    450                 455                 460

Ala Val Asp Gly Asn Trp Asn Glu Trp Ser Trp Ser Ala Cys Ser
465                 470                 475                 480

Ala Ser Cys Ser Gln Gly Arg Gln Arg Thr Arg Glu Cys Asn Gly
                485                 490                 495

Pro Ser Tyr Gly Gly Ala Glu Cys Gln Gly His Trp Val Glu Thr Arg
            500                 505                 510

Asp Cys Phe Leu Gln Gln Cys Pro Val Asp Gly Lys Trp Gln Ala Trp
        515                 520                 525
```

-continued

```
Ala Ser Trp Gly Ser Cys Ser Val Thr Cys Gly Ala Gly Ser Gln Arg
        530                 535                 540
Arg Glu Arg Val Cys Ser Gly Pro Phe Phe Gly Gly Ala Ala Cys Gln
545                 550                 555                 560
Gly Pro Gln Asp Glu Tyr Arg Gln Cys Gly Thr Gln Arg Cys Pro Glu
                    565                 570                 575
Pro His Glu Ile Cys Asp Glu Asp Asn Phe Gly Ala Val Ile Trp Lys
                580                 585                 590
Glu Thr Pro Ala Gly Glu Val Ala Val Arg Cys Pro Arg Asn Ala
            595                 600                 605
Thr Gly Leu Ile Leu Arg Arg Cys Glu Leu Asp Glu Glu Gly Ile Ala
            610                 615                 620
Tyr Trp Glu Pro Pro Thr Tyr Ile Arg Cys Val Ser Ile Asp Tyr Arg
625                 630                 635                 640
Asn Ile Gln Met Met Thr Arg Glu His Leu Ala Lys Ala Gln Arg Gly
                645                 650                 655
Leu Pro Gly Glu Gly Val Ser Glu Val Ile Gln Thr Leu Val Glu Ile
                660                 665                 670
Ser Gln Asp Gly Thr Ser Tyr Ser Gly Asp Leu Leu Ser Thr Ile Asp
            675                 680                 685
Val Leu Arg Asn Met Thr Glu Ile Phe Arg Arg Ala Tyr Tyr Ser Pro
            690                 695                 700
Thr Pro Gly Asp Val Gln Asn Phe Val Gln Ile Leu Ser Asn Leu Leu
705                 710                 715                 720
Ala Glu Glu Asn Arg Asp Lys Trp Glu Glu Ala Gln Leu Ala Gly Pro
                725                 730                 735
Asn Ala Lys Glu Leu Phe Arg Leu Val Glu Asp Phe Val Asp Val Ile
            740                 745                 750
Gly Phe Arg Met Lys Asp Leu Arg Asp Ala Tyr Gln Val Thr Asp Asn
            755                 760                 765
Leu Val Leu Ser Ile His Lys Leu Pro Ala Ser Gly Ala Thr Asp Ile
            770                 775                 780
Ser Phe Pro Met Lys Gly Trp Arg Ala Thr Gly Asp Trp Ala Lys Val
785                 790                 795                 800
Pro Glu Asp Arg Val Thr Val Ser Lys Ser Val Phe Ser Thr Gly Leu
                805                 810                 815
Thr Glu Ala Asp Glu Ala Ser Val Phe Val Val Gly Thr Val Leu Tyr
            820                 825                 830
Arg Asn Leu Gly Ser Phe Leu Ala Leu Gln Arg Asn Thr Thr Val Leu
            835                 840                 845
Asn Ser Lys Val Ile Ser Val Thr Val Lys Pro Pro Pro Arg Ser Leu
            850                 855                 860
Arg Thr Pro Leu Glu Ile Glu Phe Ala His Met Tyr Asn Gly Thr Thr
865                 870                 875                 880
Asn Gln Thr Cys Ile Leu Trp Asp Glu Thr Asp Val Pro Ser Ser Ser
                885                 890                 895
Ala Pro Pro Gln Leu Gly Pro Trp Ser Trp Arg Gly Cys Arg Thr Val
            900                 905                 910
Pro Leu Asp Ala Leu Arg Thr Arg Cys Leu Cys Asp Arg Leu Ser Thr
            915                 920                 925
Phe Ala Ile Leu Ala Gln Leu Ser Ala Asp Ala Asn Met Glu Lys Ala
            930                 935                 940
Thr Leu Pro Ser Val Thr Leu Ile Val Gly Cys Gly Val Ser Ser Leu
```

-continued

```
             945                 950                 955                 960
        Thr Leu Leu Met Leu Val Ile Ile Tyr Val Ser Val Trp Arg Tyr Ile
                         965                 970                 975
        Arg Ser Glu Arg Ser Val Ile Leu Ile Asn Phe Cys Leu Ser Ile Ile
                         980                 985                 990
        Ser Ser Asn Ala Leu Ile Leu Ile Gly Gln Thr Gln Thr Arg Asn Lys
                         995                1000                1005
        Val Val Cys Thr Leu Val Ala Ala Phe Leu His Phe Phe Phe Leu
            1010                1015                1020
        Ser Ser Phe Cys Trp Val Leu Thr Glu Ala Trp Gln Ser Tyr Met
            1025                1030                1035
        Ala Val Thr Gly His Leu Arg Asn Arg Leu Ile Arg Lys Arg Phe
            1040                1045                1050
        Leu Cys Leu Gly Trp Gly Leu Pro Ala Leu Val Val Ala Ile Ser
            1055                1060                1065
        Val Gly Phe Thr Lys Ala Lys Gly Tyr Ser Thr Met Asn Tyr Cys
            1070                1075                1080
        Trp Leu Ser Leu Glu Gly Gly Leu Leu Tyr Ala Phe Val Gly Pro
            1085                1090                1095
        Ala Ala Ala Val Val Leu Val Asn Met Val Ile Gly Ile Leu Val
            1100                1105                1110
        Phe Asn Lys Leu Val Ser Lys Asp Gly Ile Thr Asp Lys Lys Leu
            1115                1120                1125
        Lys Glu Arg Ala Gly Ala Ser Leu Trp Ser Ser Cys Val Val Leu
            1130                1135                1140
        Pro Leu Leu Ala Leu Thr Trp Met Ser Ala Val Leu Ala Val Thr
            1145                1150                1155
        Asp Arg Arg Ser Ala Leu Phe Gln Ile Leu Phe Ala Val Phe Asp
            1160                1165                1170
        Ser Leu Glu Gly Phe Val Ile Val Met Val His Cys Ile Leu Arg
            1175                1180                1185
        Arg Glu Val Gln Asp Ala Val Lys Cys Arg Val Val Asp Arg Gln
            1190                1195                1200
        Glu Glu Gly Asn Gly Asp Ser Gly Gly Ser Phe Gln Asn Gly His
            1205                1210                1215
        Ala Gln Leu Met Thr Asp Phe Glu Lys Asp Val Asp Leu Ala Cys
            1220                1225                1230
        Arg Ser Val Leu Asn Lys Asp Ile Ala Ala Cys Arg Thr Ala Thr
            1235                1240                1245
        Ile Thr Gly Thr Leu Lys Arg Pro Ser Leu Pro Glu Glu Glu Lys
            1250                1255                1260
        Leu Lys Leu Ala His Ala Lys Gly Pro Pro Thr Asn Phe Asn Ser
            1265                1270                1275
        Leu Pro Ala Asn Val Ser Lys Leu His Leu His Gly Ser Pro Arg
            1280                1285                1290
        Tyr Pro Gly Gly Pro Leu Pro Asp Phe Pro Asn His Ser Leu Thr
            1295                1300                1305
        Leu Lys Arg Asp Lys Ala Pro Lys Ser Ser Phe Val Gly Asp Gly
            1310                1315                1320
        Asp Ile Phe Lys Lys Leu Asp Ser Glu Leu Ser Arg Ala Gln Glu
            1325                1330                1335
        Lys Ala Leu Asp Thr Ser Tyr Val Ile Leu Pro Thr Ala Thr Ala
            1340                1345                1350
```

```
Thr Leu Arg Pro Lys Pro Lys Glu Pro Lys Tyr Ser Ile His
    1355            1360            1365

Ile Asp Gln Met Pro Gln Thr Arg Leu Ile His Leu Ser Thr Ala
    1370            1375            1380

Pro Glu Ala Ser Leu Pro Ala Arg Ser Pro Pro Ser Arg Gln Pro
    1385            1390            1395

Pro Ser Gly Gly Pro Pro Glu Ala Pro Pro Ala Gln Pro Pro Pro
    1400            1405            1410

Pro Pro Pro Pro Pro Pro Pro Pro Pro Gln Gln Pro Leu Pro Pro
    1415            1420            1425

Pro Pro Asn Leu Glu Pro Ala Pro Pro Ser Leu Gly Asp Pro Gly
    1430            1435            1440

Glu Pro Ala Ala His Pro Gly Pro Ser Thr Gly Pro Ser Thr Lys
    1445            1450            1455

Asn Glu Asn Val Ala Thr Leu Ser Val Ser Ser Leu Glu Arg Arg
    1460            1465            1470

Lys Ser Arg Tyr Ala Glu Leu Asp Phe Glu Lys Ile Met His Thr
    1475            1480            1485

Arg Lys Arg His Gln Asp Met Phe Gln Asp Leu Asn Arg Lys Leu
    1490            1495            1500

Gln His Ala Ala Glu Lys Asp Lys Glu Val Leu Gly Pro Asp Ser
    1505            1510            1515

Lys Pro Glu Lys Gln Gln Thr Pro Asn Lys Arg Pro Trp Glu Ser
    1520            1525            1530

Leu Arg Lys Ala His Gly Thr Pro Thr Trp Val Lys Lys Glu Leu
    1535            1540            1545

Glu Pro Leu Gln Pro Ser Pro Leu Glu Leu Arg Ser Val Glu Trp
    1550            1555            1560

Glu Arg Ser Gly Ala Thr Ile Pro Leu Val Gly Gln Asp Ile Ile
    1565            1570            1575

Asp Leu Gln Thr Glu Val
    1580
```